US011627975B2

(12) United States Patent
Ravikumar et al.

(10) Patent No.: US 11,627,975 B2
(45) Date of Patent: Apr. 18, 2023

(54) NEEDLESCOPIC INSTRUMENT WITH REUSABLE HANDLE AND DETACHABLE NEEDLE ASSEMBLY

(71) Applicant: TELEFLEX MEDICAL INCORPORATED, Morrisville, NC (US)

(72) Inventors: Sundaram Ravikumar, Briarcliff Manor, NY (US); Vikram Ravikumar, New York, NY (US); Guy Osborne, Trumbull, CT (US)

( * ) Notice: Subject to any disclaimer, the term of this patent is extended or adjusted under 35 U.S.C. 154(b) by 246 days.

(21) Appl. No.: 16/747,113

(22) Filed: Jan. 20, 2020

(65) Prior Publication Data

US 2020/0197035 A1 Jun. 25, 2020

Related U.S. Application Data

(63) Continuation of application No. 14/784,886, filed as application No. PCT/US2014/034397 on Apr. 16, 2014, now Pat. No. 10,537,347.

(60) Provisional application No. 61/812,691, filed on Apr. 16, 2013.

(51) Int. Cl.
*A61B 17/29* (2006.01)
*A61B 17/34* (2006.01)
*A61B 17/00* (2006.01)

(52) U.S. Cl.
CPC .......... *A61B 17/29* (2013.01); *A61B 17/3496* (2013.01); *A61B 2017/0046* (2013.01); *A61B 2017/00991* (2013.01); *A61B 2017/2919* (2013.01)

(58) Field of Classification Search
CPC ................ A61B 17/29; A61B 17/3496; A61B 2017/0046; A61B 2017/00991; A61B 2017/2919; A61B 17/28; A61B 2017/00473; A61B 2017/00469; A61B 2017/00464; A61B 18/1445; A61B 18/1447

See application file for complete search history.

(56) References Cited

U.S. PATENT DOCUMENTS

| | | | |
|---|---|---|---|
| 4,655,750 | A | 4/1987 | Vaillancourt |
| 5,201,742 | A | 4/1993 | Hasson |
| 5,282,800 | A | 2/1994 | Foshee et al. |
| 5,413,561 | A | 5/1995 | Fischell et al. |
| 5,454,790 | A | 10/1995 | Dubrul |
| 5,456,673 | A | 10/1995 | Ziegler et al. |
| 5,505,710 | A | 4/1996 | Dorsey, III |
| 5,626,597 | A | 5/1997 | Urban et al. |
| 5,658,272 | A | 8/1997 | Hasson |
| 5,759,188 | A | 6/1998 | Yoon |

(Continued)

FOREIGN PATENT DOCUMENTS

| | | |
|---|---|---|
| CN | 1695566 A | 11/2005 |
| CN | 101586725 A | 11/2009 |

(Continued)

*Primary Examiner* — Diane D Yabut
(74) *Attorney, Agent, or Firm* — BakerHostetler

(57) ABSTRACT

A surgical device may include a disposable needle assembly, a reusable handle assembly, and a retractable slide. The handle assembly may include a ratchet mechanism, a locking mechanism, an arming mechanism, and a cage. A method for inserting and releasing the disposable needle assembly from the reusable handle assembly is also disclosed herein.

20 Claims, 26 Drawing Sheets

(56) References Cited

U.S. PATENT DOCUMENTS

| | | |
|---|---|---|
| 5,868,714 A | 2/1999 | Danks |
| 6,159,224 A | 12/2000 | Yoon |
| 6,197,002 B1 | 3/2001 | Peterson |
| 6,224,569 B1 | 5/2001 | Brimhall |
| 6,336,914 B1 | 1/2002 | Gillespie, III |
| 7,766,937 B2 | 8/2010 | Ravikumar |
| 8,133,255 B2 | 3/2012 | Ravikumar |
| 8,230,863 B2 | 7/2012 | Ravikumar et al. |
| 8,313,507 B2 | 11/2012 | Ravikumar |
| 8,956,351 B2 | 2/2015 | Ravikumar et al. |
| 9,326,784 B2 | 5/2016 | Ravikumar |
| 9,486,238 B2 | 11/2016 | Ravikumar et al. |
| 9,492,187 B2 | 11/2016 | Ravikumar et al. |
| 10,166,038 B2 | 1/2019 | Ravikumar et al. |
| 10,368,907 B2 | 8/2019 | Ravikumar et al. |
| 10,390,852 B2 | 8/2019 | Ravikumar et al. |
| 10,537,347 B2 | 1/2020 | Ravikumar et al. |
| 2003/0130693 A1 | 7/2003 | Levin et al. |
| 2003/0181858 A1 | 9/2003 | Lajtai et al. |
| 2006/0074374 A1 | 4/2006 | Gresham |
| 2007/0088277 A1 | 4/2007 | McGinley et al. |
| 2007/0093755 A1 | 4/2007 | Koos et al. |
| 2007/0093790 A1 | 4/2007 | Downey et al. |
| 2007/0250112 A1 | 10/2007 | Ravikumar et al. |
| 2007/0282170 A1 | 12/2007 | Ravikumar |
| 2008/0215078 A1 | 9/2008 | Bennett |
| 2009/0247900 A1 | 10/2009 | Zimmer |
| 2010/0016884 A1 | 1/2010 | Ravikumar |
| 2010/0222747 A1 | 9/2010 | Wenchell et al. |
| 2010/0292724 A1 | 11/2010 | Ravikumar et al. |
| 2011/0046449 A1 | 2/2011 | Minnelli et al. |
| 2011/0160538 A1 | 6/2011 | Ravikumar et al. |
| 2011/0196205 A1 | 8/2011 | Hathaway et al. |
| 2012/0080483 A1 | 4/2012 | Riestenberg et al. |
| 2012/0277576 A1 | 11/2012 | Lui |
| 2014/0276666 A1* | 9/2014 | Malkowski ............ A61B 17/29 606/1 |
| 2017/0156789 A1 | 6/2017 | Ravikumar et al. |
| 2017/0224413 A1 | 8/2017 | Ravikumar et al. |

FOREIGN PATENT DOCUMENTS

| | | |
|---|---|---|
| CN | 102510739 A | 6/2012 |
| EP | 0647429 A2 | 4/1995 |
| EP | 1516592 A2 | 3/2005 |
| JP | 58133348 U | 9/1983 |
| JP | 02-015159 | 1/1990 |
| JP | 09-512732 | 12/1997 |
| JP | 2003510137 A | 3/2003 |
| JP | 2008253585 A | 10/2008 |
| JP | 2009-529983 | 8/2009 |
| JP | 2010207260 A | 9/2010 |
| JP | 2011212458 A | 10/2011 |
| JP | 2012165958 A | 9/2012 |
| JP | 2013106771 A | 6/2013 |
| JP | 2013-248222 A | 12/2013 |
| WO | 97/14457 A1 | 4/1997 |
| WO | 2007050969 A2 | 5/2007 |
| WO | 2012044815 A1 | 4/2012 |

* cited by examiner

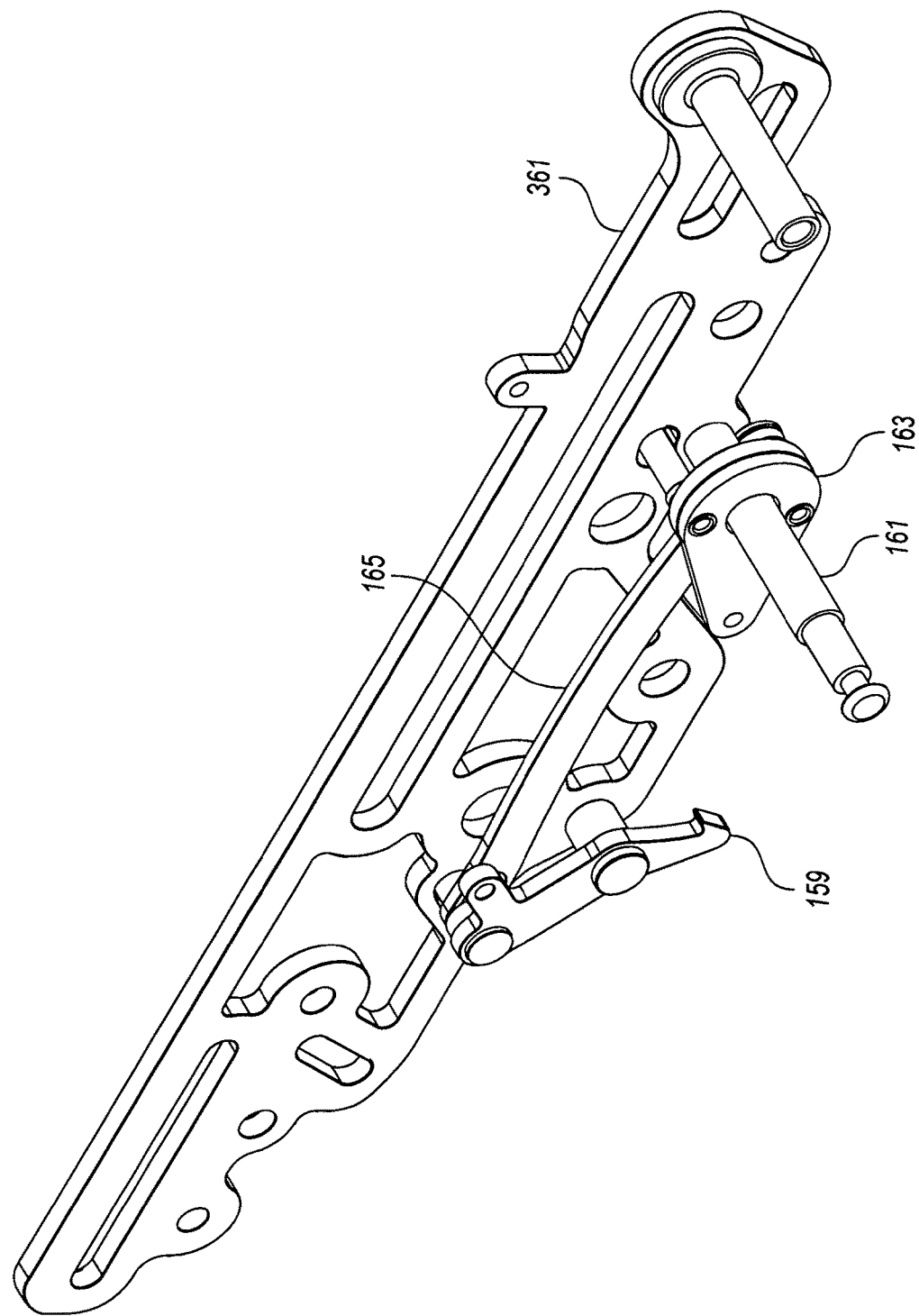

NEEDLESCOPIC INSTRUMENT WITH REUSABLE HANDLE AND DETACHABLE NEEDLE ASSEMBLY

CROSS-REFERENCE TO RELATED APPLICATIONS

The present application is a continuation application of U.S. application Ser. No. 14/784,886, filed Oct. 15, 2015, which in turn claims the priority of International Application PCT/US2014/034397, filed Apr. 16, 2014, which in turn claims the benefit of Provisional Application No. 61/812,691, filed Apr. 16, 2013. The entire contents of which are hereby incorporated by reference in their entirety.

BACKGROUND OF THE INVENTION

1. Field of the Invention

The present invention relates to surgical instruments and methods of their use, and more particularly, to minimally invasive surgical instruments incorporating a needle and a working tool disposed within and configured to extend and retract from the needle tip.

2. Description of Related Art

Over the last two decades, minimally invasive surgery has become the standard for many types of surgeries which were previously accomplished through open surgery. Minimally invasive surgery generally involves introducing an optical element (e.g., laparoscopic or endoscope) through a surgical or natural port in the body, advancing one or more surgical instruments through additional ports or through the endoscope, conducting the surgery with the surgical instruments, and withdrawing the instruments and scope from the body. In laparoscopic surgery (broadly defined herein to be any surgery where a port is made via a surgical incision, including but not limited to abdominal laparoscopy, arthroscopy, spinal laparoscopy, etc.), a port for a scope is typically made using a surgical trocar assembly.

The trocar assembly often includes a port, a sharp pointed element (trocar) extending through and beyond the distal end of the port, and at least in the case of abdominal laparoscopy, a valve on the proximal portion of the port. Typically, a small incision is made in the skin at a desired location in the patient. The trocar assembly, with the trocar extending out of the port, is then forced through the incision, thereby widening the incision and permitting the port to extend through the incision, past any facie, and into the body (cavity). The trocar is then withdrawn, leaving the port in place. In certain circumstances, an insufflation element may be attached to the trocar port in order to insufflate the surgical site. An optical element may then be introduced through the trocar port. Additional ports are then typically made so that additional laparoscopic instruments may be introduced into the body.

Trocar assemblies are manufactured in different sizes. Typical trocar port sizes include 5 mm, 10 mm, and 12 mm, which are sized to permit variously sized laparoscopic instruments to be introduced therethrough including, e.g., graspers, dissectors, staplers, scissors, suction/irrigators, clamps, forceps, biopsy forceps, etc. While 5 mm trocar ports are relatively small, in some circumstances where internal working space is limited (e.g., children), it is difficult to place multiple 5 mm ports in the limited area. In addition, 5 mm trocar ports tend to limit movement of instruments inside the abdominal cavity to a great extent.

Further, while laparoscopic surgery has reduced the trauma associated with various surgical procedures and has concomitantly reduced recovery time from these surgeries, there always remains a desire in the art to further reduce the trauma to the patient. One area of trauma associated with laparoscopic surgery identified by the inventor hereof as being susceptible of reduction are the scars which result from the trocar ports used. In many laparoscopic surgeries, three or more trocar incisions are made. For example, in laparoscopic hernia repair surgery, four trocar incisions are typically made, with one incision for insufflating the abdomen and inserting the optical device, two incisions for trocar ports for inserting graspers therethrough, and a fourth port for passing a stapler therethrough. Those skilled in the art and those who have undergone surgical procedures are aware that even the 5 mm trocar ports leave holes which must be stitched and which result in scars. Scar tissue may affect the internal portion of the facia as well as the cosmetic appearance of the skin, which may be detrimental for the patient or even a surgeon if that area of the skin is subject to a later incision or medical procedure.

A second area of trauma associated with laparoscopic surgery relates to trauma resulting from the manipulation (e.g., angling) of the trocar ports required in order to conduct the surgery due to inexact placement. Angling of the port can cause tearing at the incision periphery. Such tearing can lead to extensive scar tissue and in general an extension of the incision area.

There continues to be a need in the art for lower cost laparoscopic tools and surgical assemblies which have improved applications, reduce trauma to the patient, reduce complications to the patient, do not lead to extension of the incision area, do not lead to increased scar tissue generation, are easy to make and use, and improve safety while reducing costs to health care providers and patients and reducing the surgical time for a procedure which in turn may reduce costs and complications. The inventive device includes a reusable handle assembly which can be actuated with various needle assemblies of varying diameters and end effectors. Thus the same inventive device may have many different uses within one surgical procedure. These and other needs are met by the inventive device and method.

Other advantages of the present invention will become apparent from the following description and appended claims.

BRIEF DESCRIPTION OF THE DRAWINGS

FIG. 13A is a perspective of a ratchet mechanism embodiment of the reusable handle assembly of the present invention.

DETAILED DESCRIPTION OF THE PREFERRED EMBODIMENTS

Figure 1:
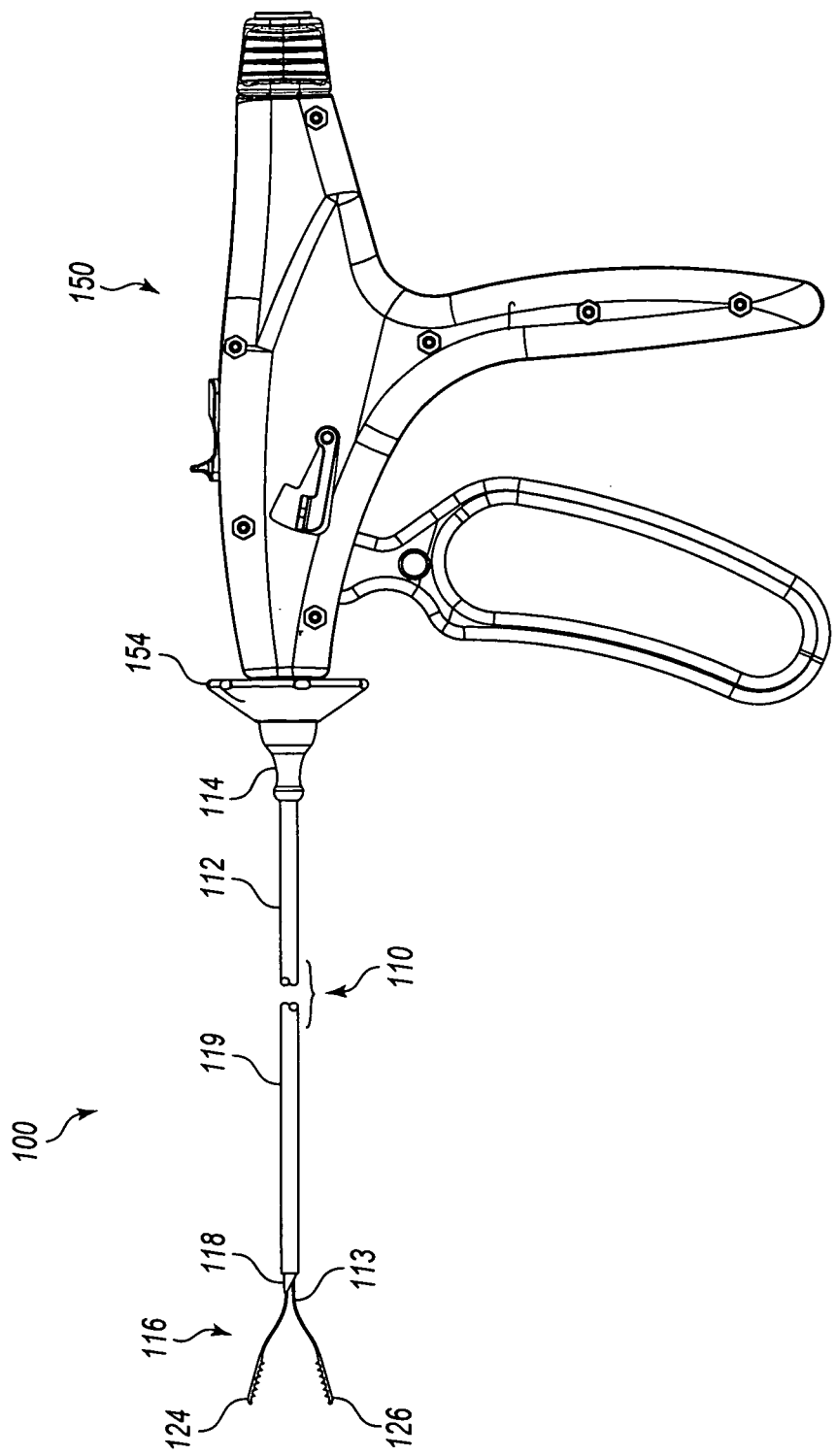
FIG. 1 is one embodiment of an actuated device of the present invention with the graspers in a retracted position.

Reference will now be made to the drawings wherein like reference numerals identify similar structural features or aspects of the subject invention. For purposes of explanation and illustration, and not limitation, exemplary embodiments of a minimally invasive surgical assembly in accordance with the invention, or aspects thereof, are shown in FIGS. 1-19D. The surgical assembly of the invention is a low cost, easy to manufacture, medical device which can be used, for example, during minimally invasive surgical procedures to reduce trauma to a patient.

Examples of minimally invasive surgical assemblies and related equipment are described in U.S. Pat. No. 7,766,937 to Ravikumar, U.S. Pat. No. 8,230,863 to Ravikumar et al., U.S. Pat. No. 8,313,507 to Ravikumar, U.S. Pat. No. 8,133,255 to Ravikumar et al., U.S. patent application Ser. No. 11/685,522 to Ravikumar et al (published as U.S. Patent Pub. No. 2007/0250112), U.S. patent application Ser. No. 12/503,035 to Ravikumar (published as U.S. Patent Pub. No. 2010/0016884), U.S. patent application Ser. No. 12/689,352 to Ravikumar et al (published as U.S. Patent Pub. No. 2010/0292724), U.S. patent application Ser. No. 11/610,746 to Ravikumar et al (published as U.S. Patent Pub. No. 2007/0282170), and U.S. patent application Ser. No. 12/689,352 to Ravikumar et al (published as U.S. Patent Pub. No. 2010/0292724), all of which patents, applications, and publications are incorporated by reference herein in their entireties.

Figure 2:
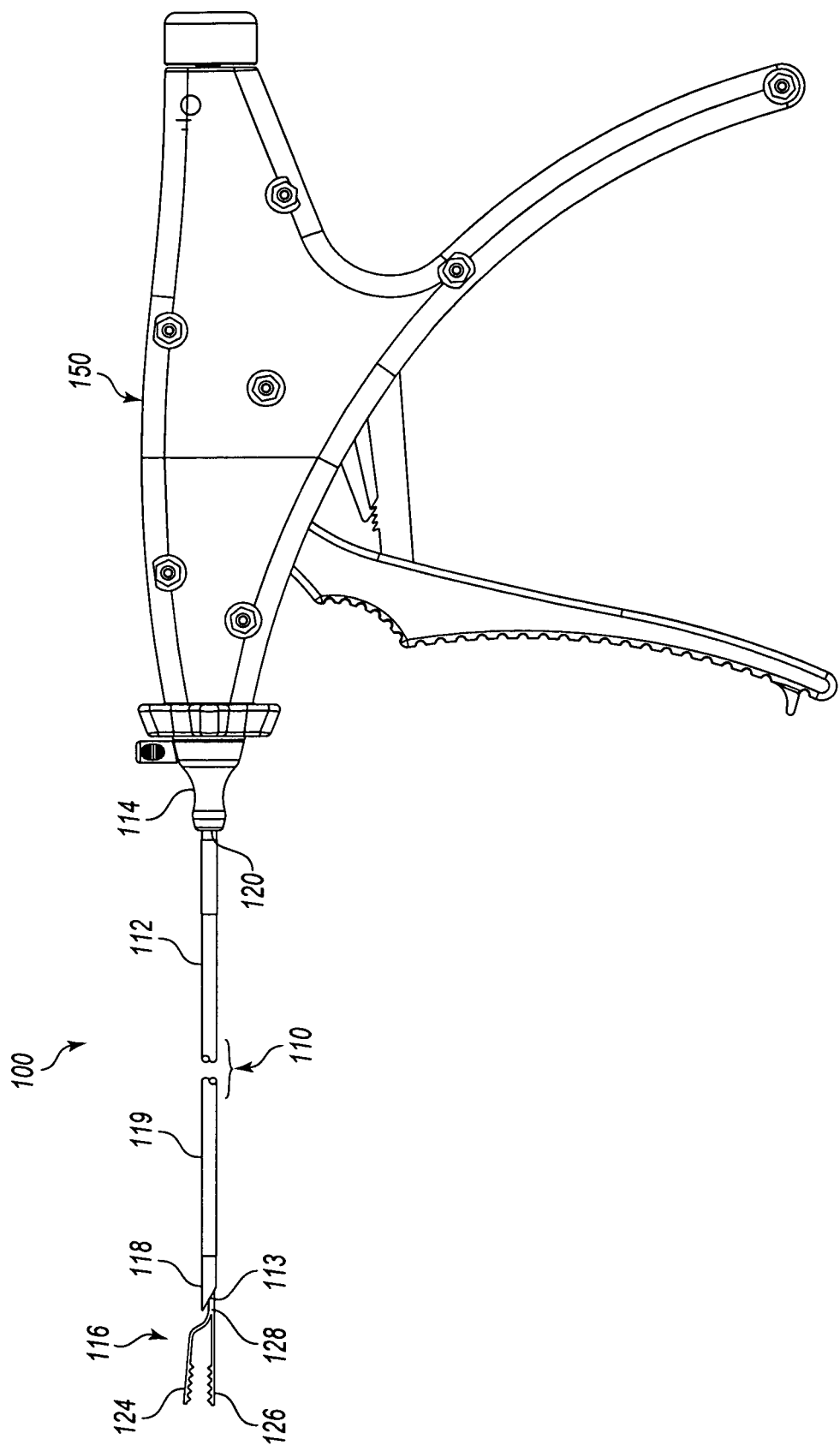
FIG. 2 is an embodiment of an unactuated device of the present invention with the graspers in an open position.
Figure 3:
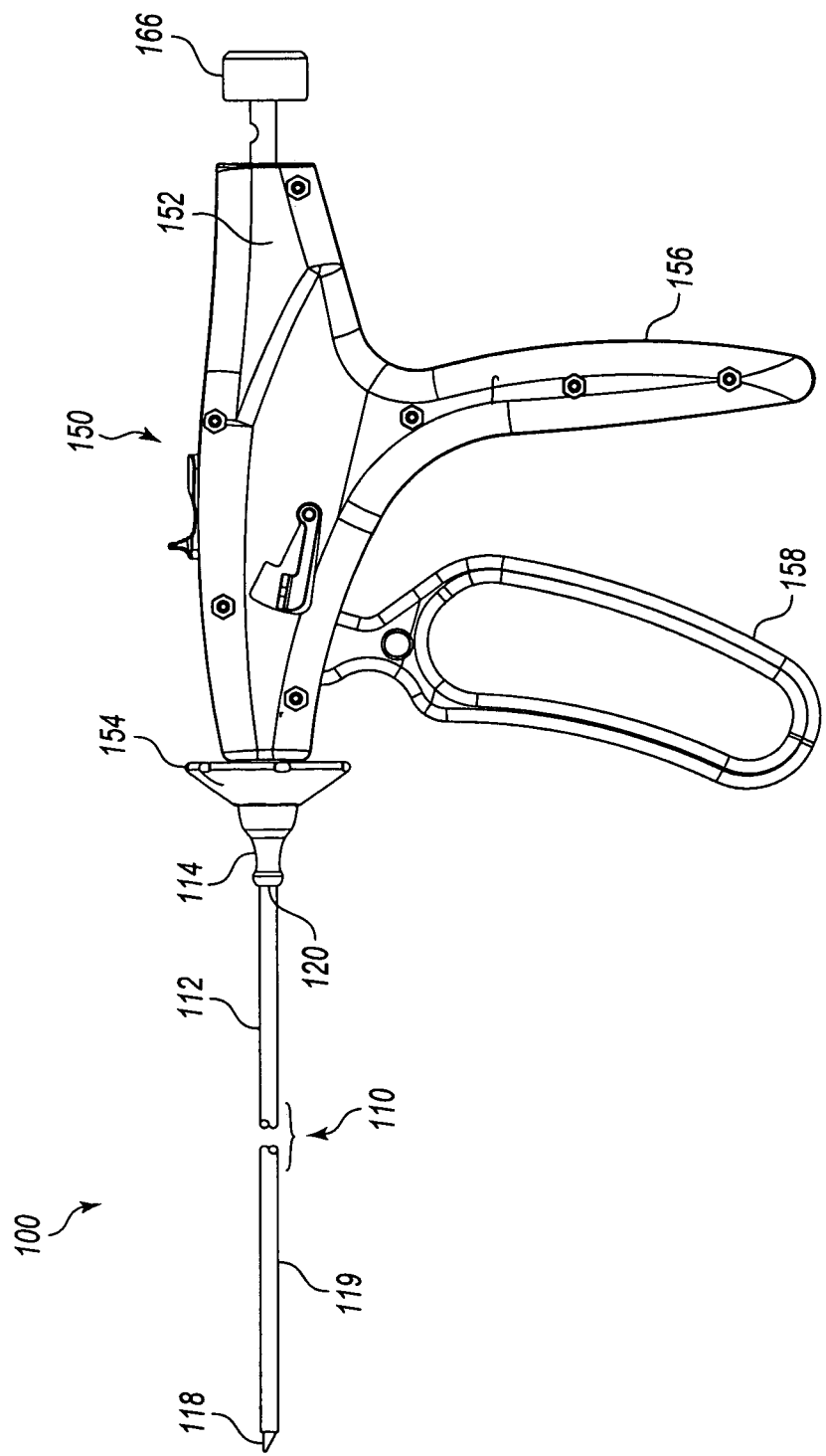
FIG. 3 is an embodiment of an actuated device of the present invention with the grasper in a closed position.
Figure 4:
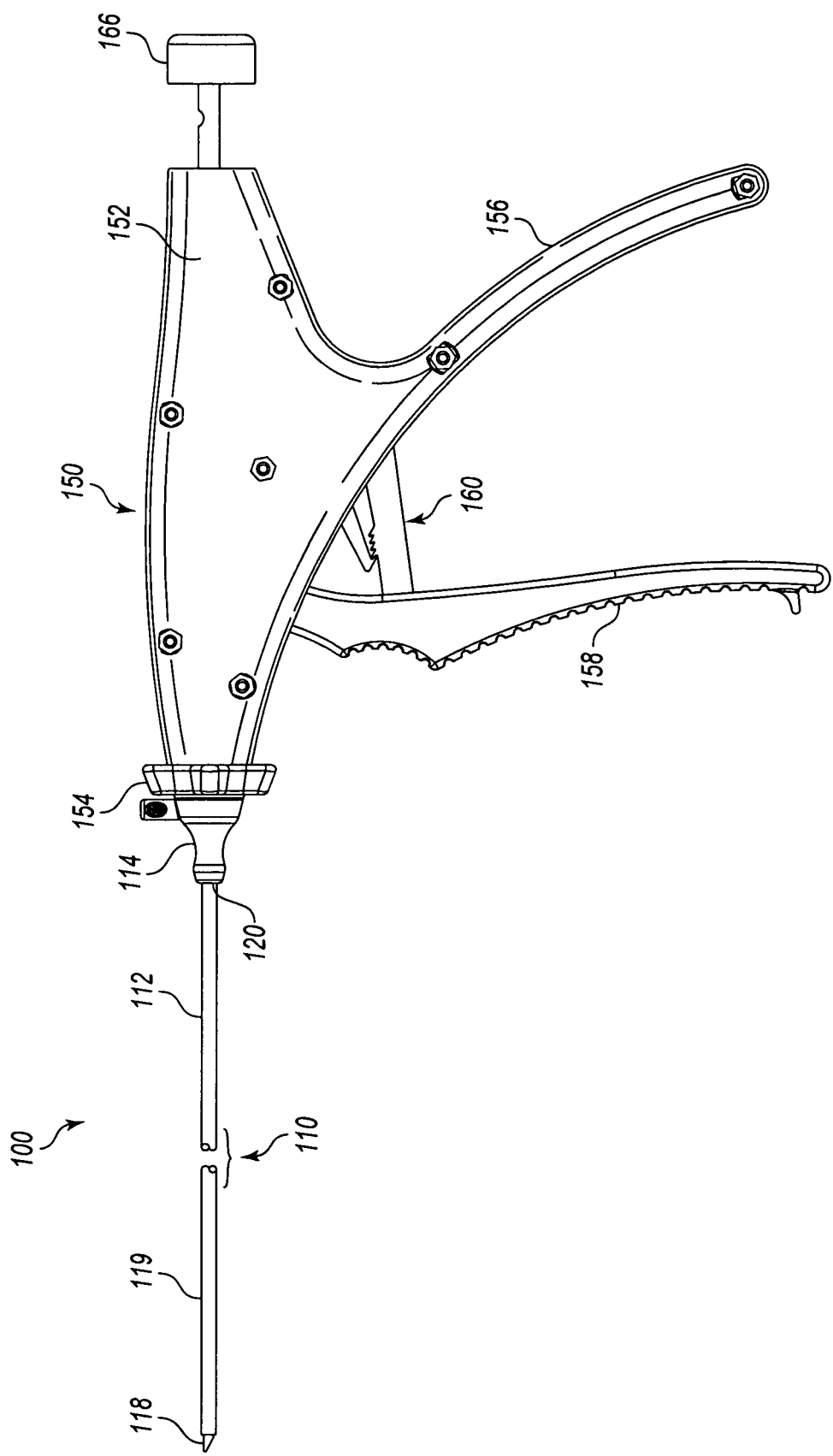
FIG. 4 is an embodiment of the reusable handle assembly of the unactuated device of the present invention.
Figure 5:
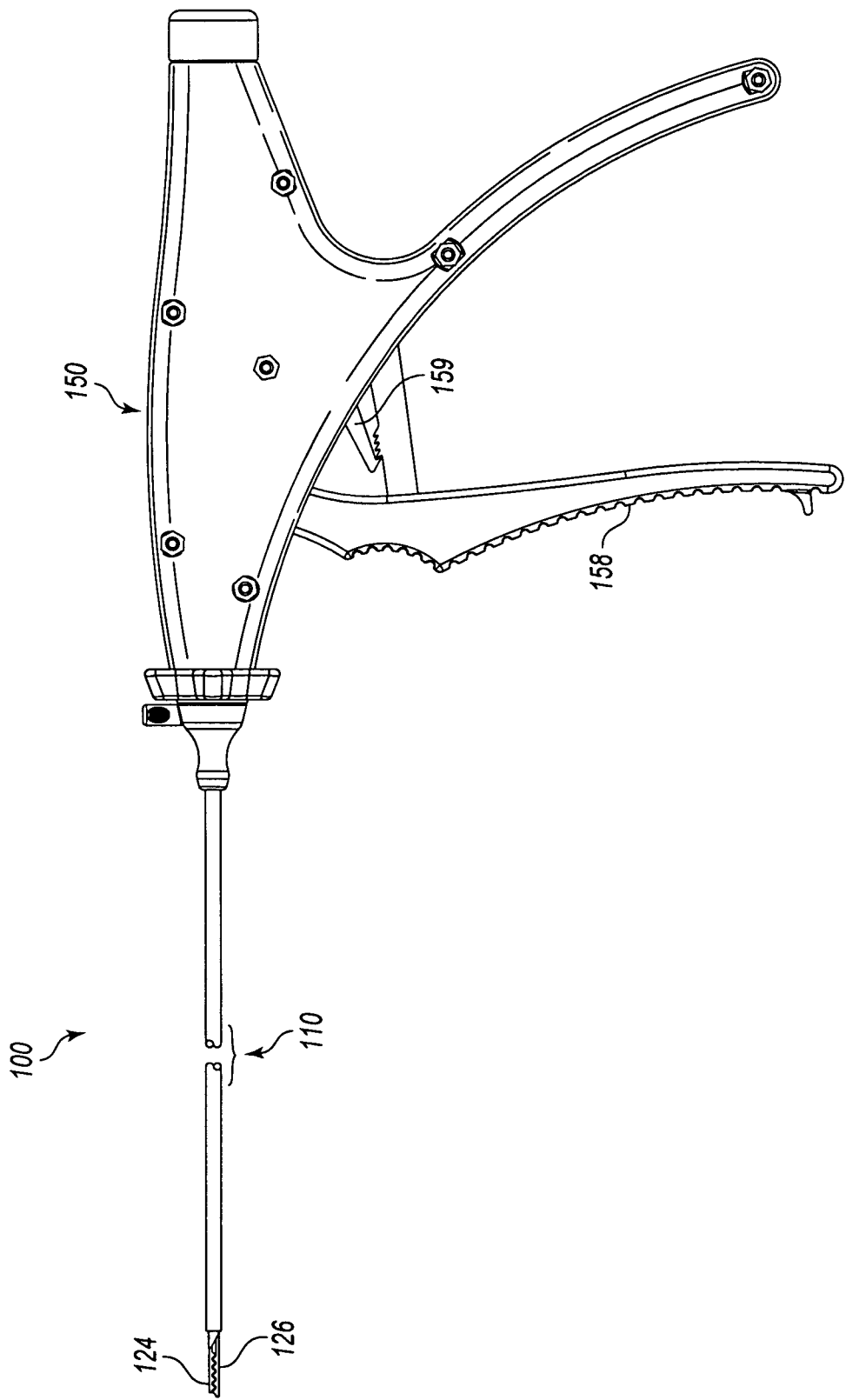
FIG. 5 is an embodiment of the reusable handle assembly of the actuated device of the present invention.
Figure 15:
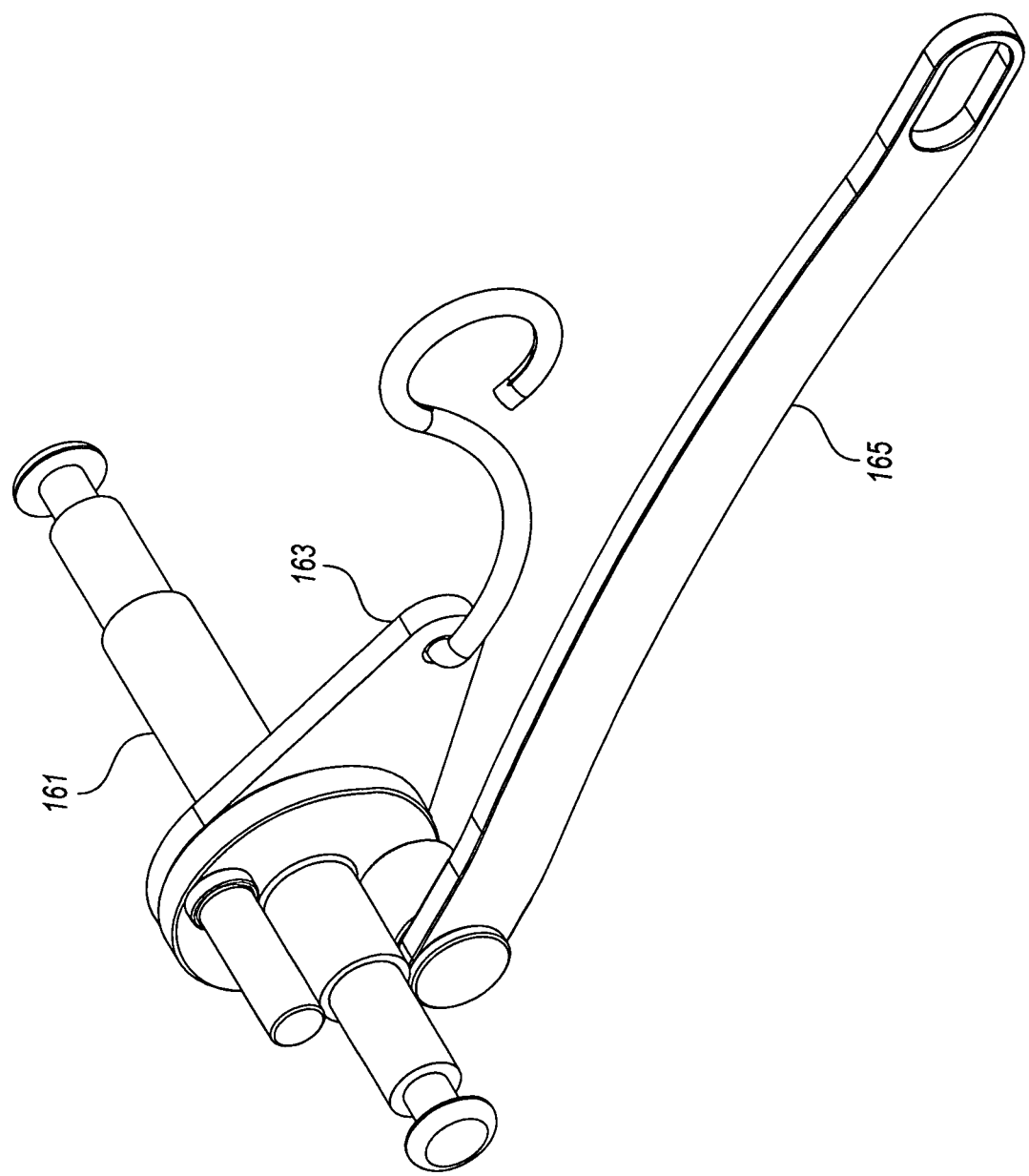
FIG. 15 is an exploded view of a ratchet mechanism embodiment of the reusable handle assembly of the present invention.

Referring now to FIG. 15, a surgical device 100 is shown which includes a disposable needle assembly 110 and two embodiments of a reusable handle assembly 150 operatively associated therewith. FIGS. 1 and 3 show one embodiment of the reusable handle assembly 150 while FIGS. 2, 4, and 5 show another embodiment of the reusable handle assembly 150. In general, the reusable handle assembly 150 is preferably configured and adapted to receive the disposable needle assembly 110, manipulate it during a surgical procedure, and release it for disposal.

The disposable needle assembly 110 is preferably configured and adapted to be advanced into the reusable handle assembly 150, set into position, and operated for one time use. The disposable needle assembly 110 is also preferably configured and adapted to prevent reprocessing thereof once used, and may be provided with a 2.4 mm needle or a 5 mm needle. The reusable handle assembly 150 is preferably configured and adapted to receive, operate, and release the disposable needle assembly 110 regardless of whether a 2.4 mm needle is provided for insertion percutaneously under direct visualization without the use of a trocar, or whether a 5 mm needle is provided for use with a trocar during laparoscopic procedures. In this manner, the surgical device 100 allows for improved management and control of the assemblies thereof, reduces costs to health care providers, and prevents unauthorized reprocessing and selling of needle assemblies without MLT certification.

As shown in FIG. 1, disposable needle assembly 110 includes an elongated needle member 112, a needle hub 114 which detachably couples and is longitudinally fixed to the handle assembly 150, and a grasping assembly 116 operatively associated with a lumen 113 defined by elongated needle member 112. Elongated needle member 112 and grasping assembly 116 are selectively longitudinally translatable relative to one another and relative to needle hub 114 and handle assembly 150 via user manipulation of handle assembly 150.

Figure 6:
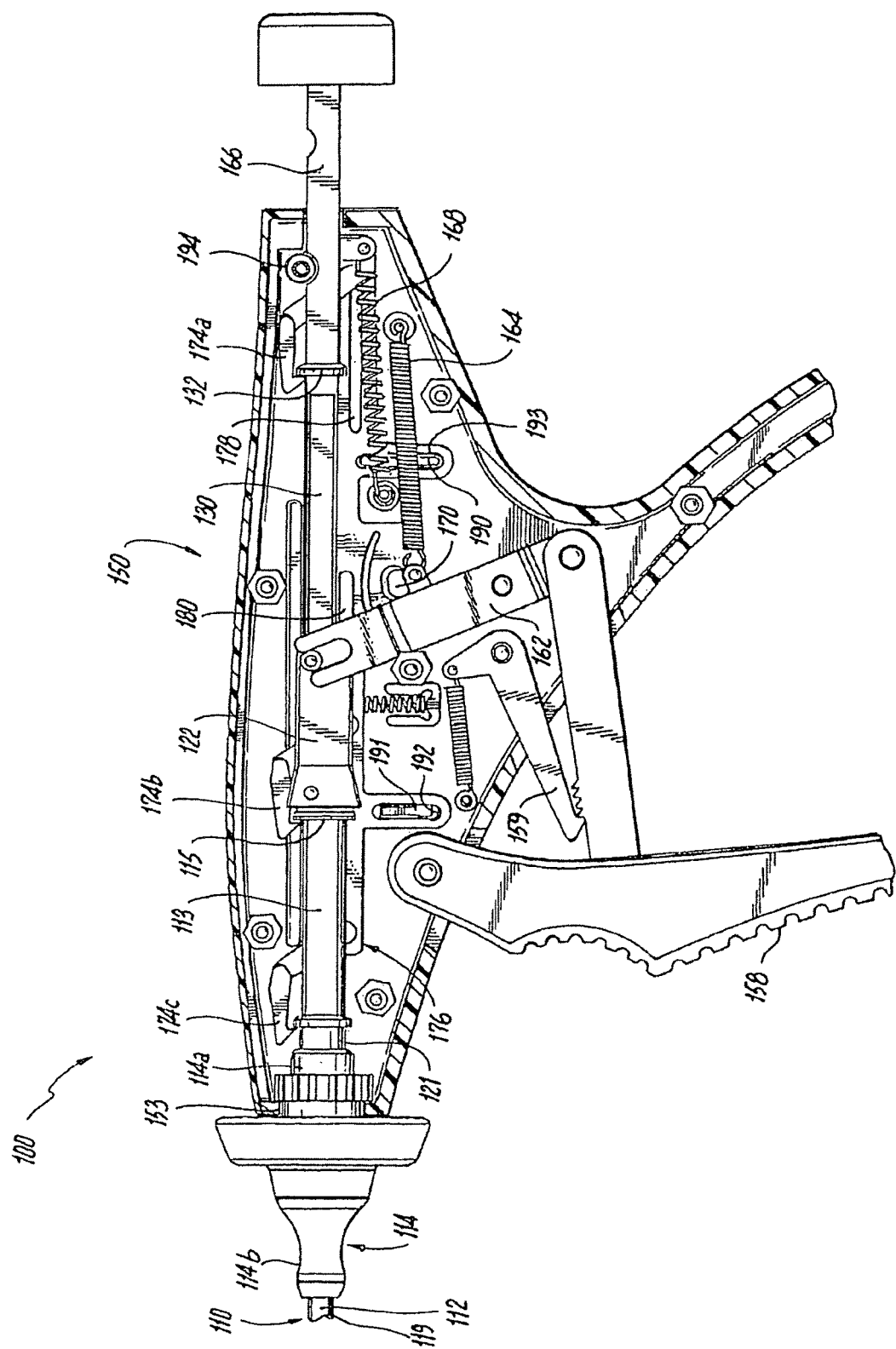
FIG. 6 is an embodiment of the reusable handle assembly of a system of the actuated device of the present invention.

Elongated needle member 112 includes a sharpened distal tip portion 118, a needle shaft 119 having an inner surface which defines lumen 113 through which grasping assembly 116 longitudinally translates. Needle shaft 119 extends through a lumen 120 defined by needle hub 114, and into the interior of the handle assembly 150 as shown in FIG. 6. Continuing with FIG. 6, needle shaft 119 of needle member 112 extends through proximal and distal portions 114a, 114b of needle hub 114, and couples to proximal member 130. Proximal member 130 has a proximal head 115 of enlarged diameter which interfaces to sliding shaft 122 of the handle assembly 150. As shown, sliding shaft 122 is coupled to a trigger 158 of handle assembly 150. In this manner, trigger 158 is retractable to distally longitudinally translate sliding shaft 122 of handle assembly 150 and proximal member 130 of needle member 112 relative to grasping assembly 116.

As shown in FIG. 1, grasping assembly 116 includes a pair of end effectors (e.g., upper and lower arms) 124, 126 coupled to or integrally formed with a shaft 128 having an outer surface profile corresponding to the inner surface of the needle shaft 119. Upper and lower arms 124, 126 are preferably biased radially outward from the longitudinal axis of shaft 128, but can also be provided as one or more hinged jaws or other surgical tools such as those described in the above referenced patents and publications incorporated by reference herein. Shaft 128 extends through lumen 113 along the length of the needle shaft 119, through needle hub 114, and into the interior of the handle assembly 150 as shown in FIG. 6. Shaft 128 of grasping assembly 116 is coupled to a proximal member 130 having a proximal end 132. Proximal member 130 is selectively longitudinally translatable within the lumen 113 of elongated needle member 112, and within the sliding shaft 122 of handle assembly 150 via user manipulation of a retractable slide of the handle assembly 150 (further discussed below). The retractable slide of the handle assembly 150 interfaces to proximal end 132 to translate shaft 128 and arms 124, 126 of grasping assembly 116 relative to elongated needle member 112.

Figure 10:
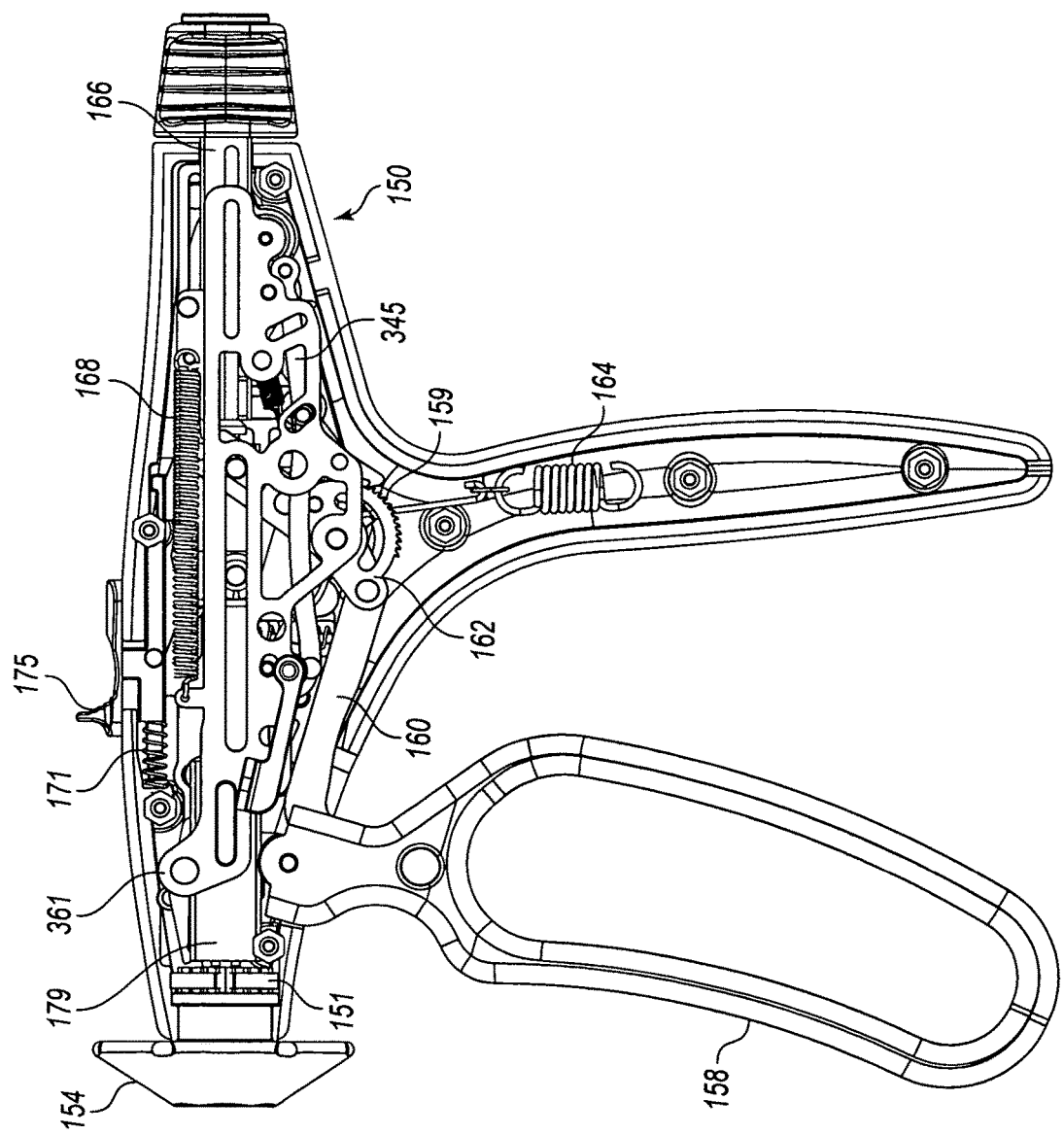
FIG. 10 is an embodiment of the reusable handle assembly of the present invention.
Figure 12A:
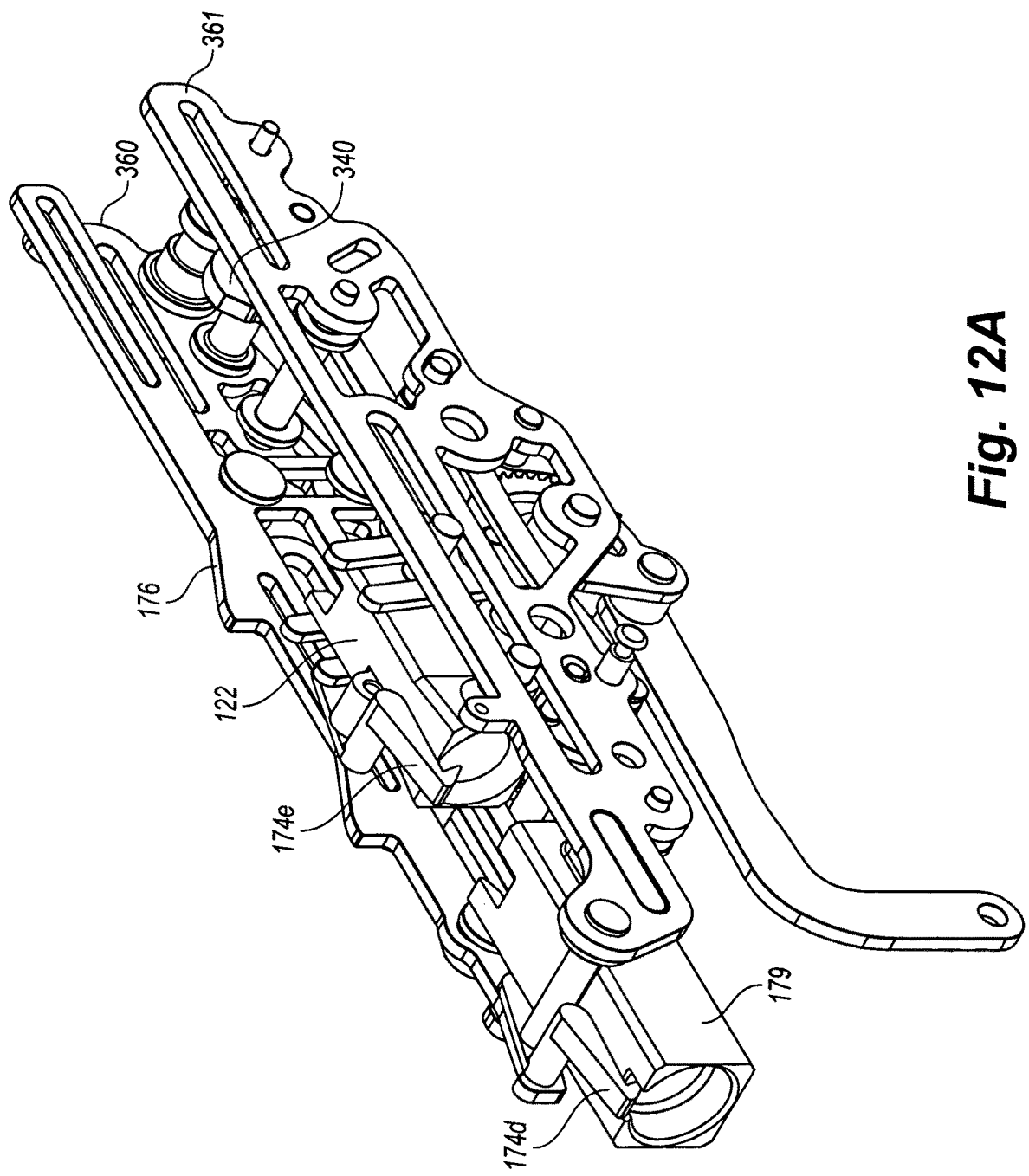
FIG. 12A is a perspective of a cage assembly embodiment of the reusable handle assembly of the present invention.

Proximal member 130 preferably has a cross-section which defines an interference fit with interior surfaces of the lumen 113 of elongated needle member 112 to rotatably fix elongated needle member 112 to grasping assembly 116. For example, the lumen 113 may define a rectangular cross section and proximal member 130 may also define a rectangular cross section along at least a portion thereof which can longitudinally translate within proximal member 130, yet which cannot rotate relative thereto. Needle hub 114 also preferably defines lumen 120 in a manner which allows longitudinal translation of needle shaft 119 relative to needle hub 114, yet which rotatably fixes needle hub 114 to needle shaft 119. Certain embodiments of such rotational limits are shown in FIGS. 10 and 12A.

As further discussed below with respect to the handle assembly 150, such structure facilitates rotation of needle member 112, needle hub 114, and grasping assembly 116 together independent of handle assembly 150, as well as longitudinal advancement of the needle member 112 over the grasping assembly 116, all by user manipulation of handle assembly 150.

As shown in FIGS. 1-5, handle assembly 150 includes a housing 152 for storing and protecting the components thereof, a rotation hub 154 for rotating the elongated needle member 112, needle hub 114, and grasping assembly 116, and a proximal handle member 156, a distal trigger 158, and a drive link 160 for actuating distal longitudinal translation of the elongated needle member 112 relative to the grasping assembly 116. Such distal translation causes the disposable assembly 110 to move from the open configuration shown in FIG. 1 to the closed configuration shown in FIG. 5 as the needle member 112 is forced over at least a portion of the arms 124, 126. The grasping assembly 116 may further be covered by the needle or sharpened distal tip portion 118 as shown in FIG. 3.

FIGS. 1-5 also show the grasping assembly 116 in different stages of actuation. In FIG. 1 the grasping assembly has open arms 124, 126 compared to FIG. 2 where arm 124 is open but arm 126 is semi-closed and compared to FIG. 5 where arms 124, 126 are closed but the distal tip 118 of the needle has not been pushed over the grasping assembly 118 such that in use the grasping assembly 118 is grasping a material such as tissue, a blood vessel or organ.

Continuing with FIG. 6, handle assembly 150 further includes a crank assembly 162 for coupling trigger 158 to sliding shaft 122 of handle assembly 150, and a primary return spring 164 for biasing sliding shaft 122 proximally and trigger 158 distally toward the configuration of FIG. 2 in which the arms 124, 126 of the grasping assembly 116 are extended relative to the needle member 112 and open.

Figure 7:
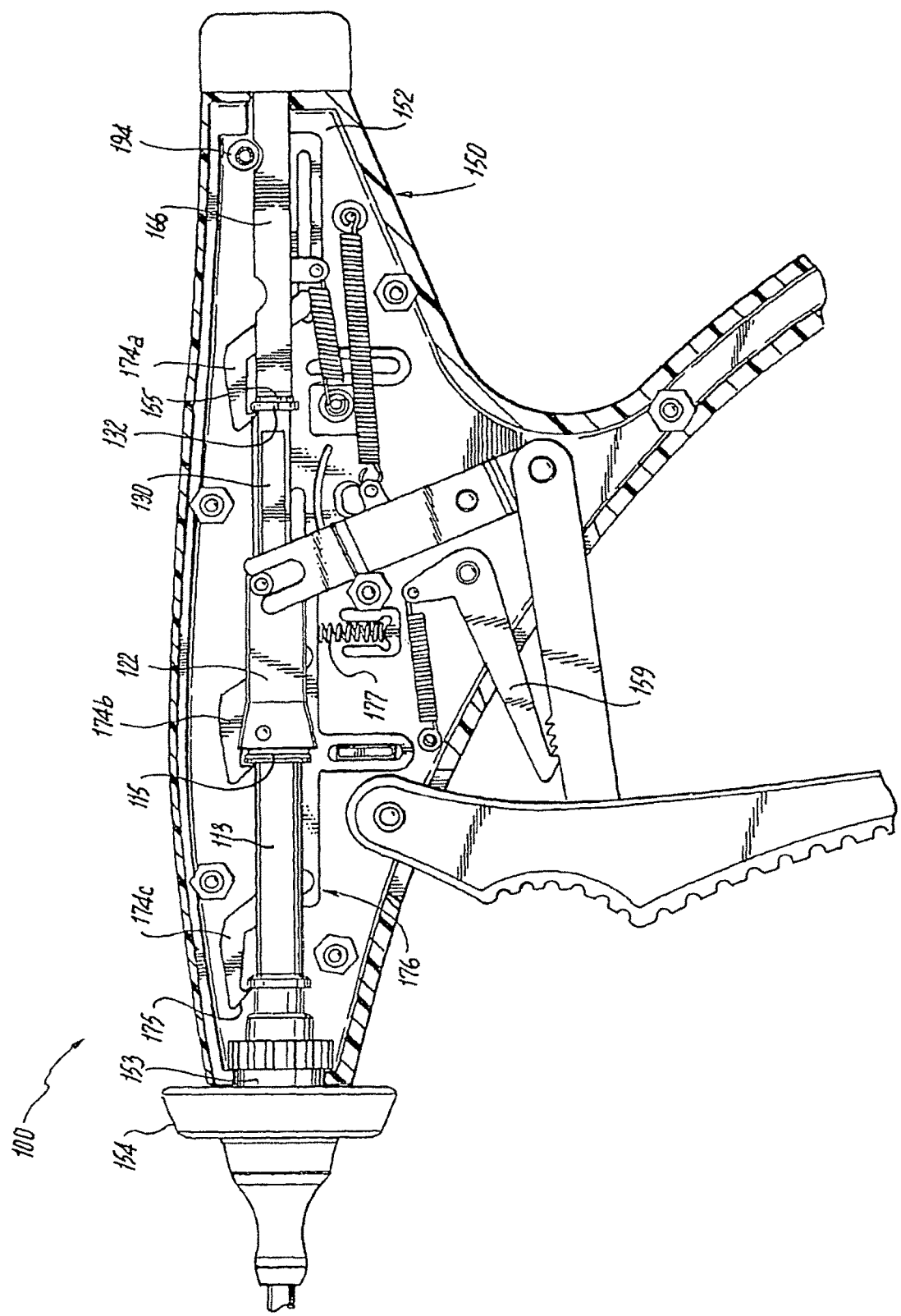
FIG. 7 is an embodiment of the reusable handle assembly of a system of the actuated device of the present invention.
Figure 8:
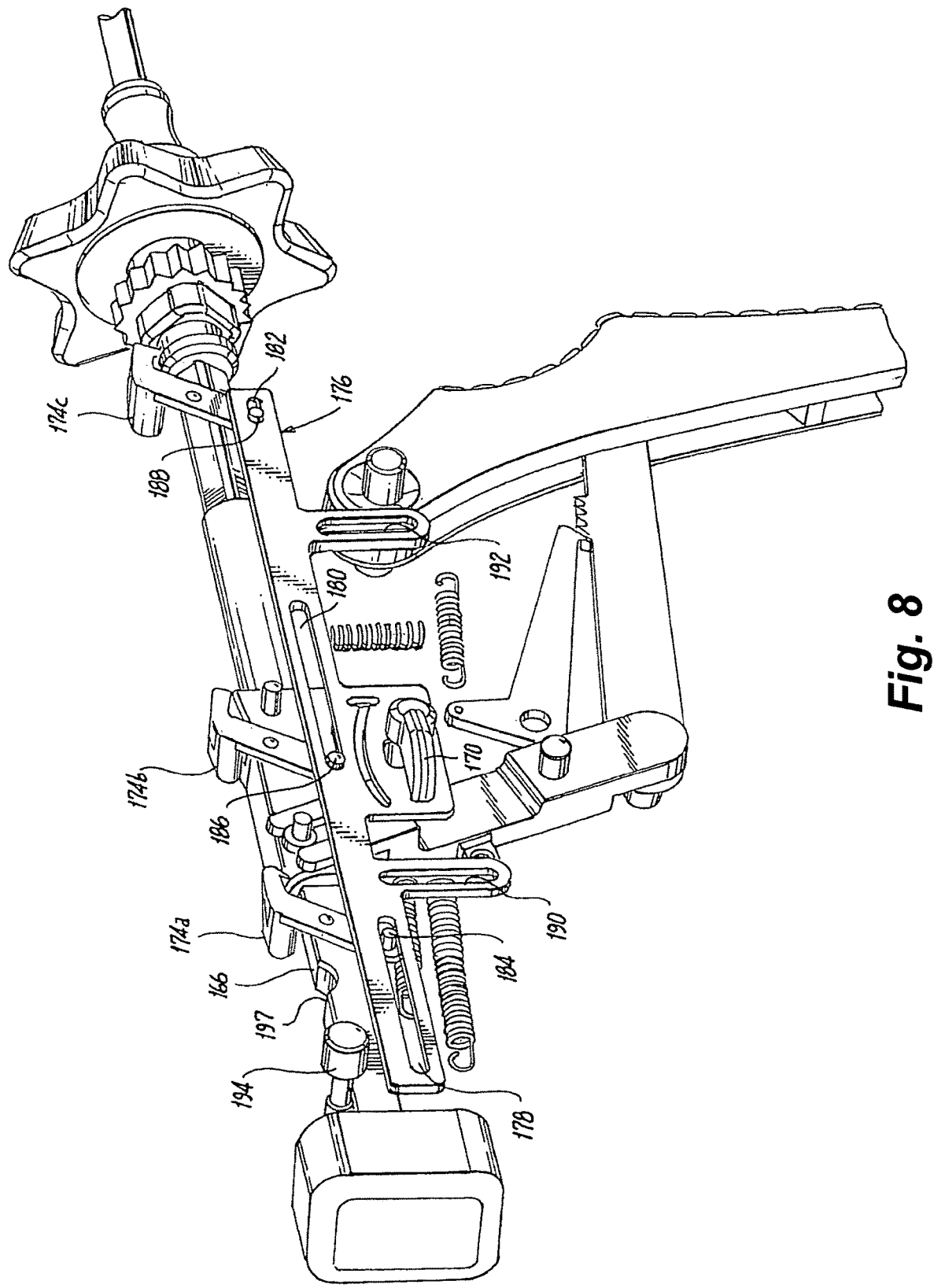
FIG. 8 is an embodiment of an arm slide of the present invention.
Figure 9:
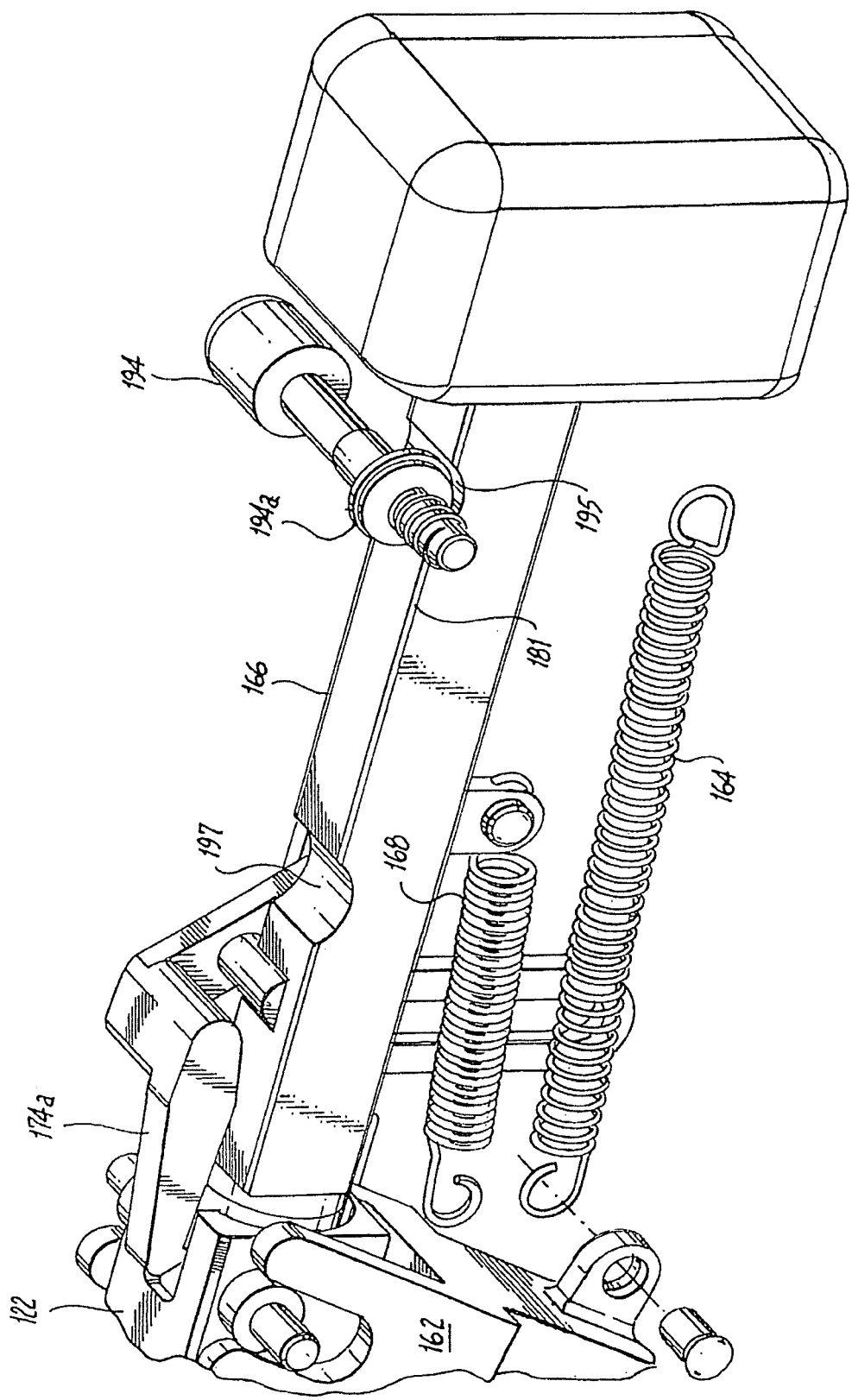
FIG. 9 is an embodiment of a button assembly of the present invention.

Handle assembly 150 also includes an arm slide 166 for manipulating elongated needle member 112, a secondary return spring 168 for biasing arm slide 166 distally toward the position shown in FIG. 7 (which corresponds to the configuration of FIG. 2). Handle assembly 150 also includes a release lever 170 for allowing release of disposable needle assembly 110 from handle assembly 150, and a latch assembly for receiving, positioning, operating, and releasing elongated needle member 112 from handle assembly 150. The latch assembly includes latches 174a, 174b, 174c, and release bar 176, which, in conjunction with release lever 170, operate to vertically raise and lower latches 174a, 174b, 174c to receive and release the disposable assembly 110. The release lever does not need to move to receive a disposable assembly.

More particularly, latches 174a, 174b, 174c respectively couple to proximal end 132 of proximal member 130 of grasping assembly 116, proximal end 115 of proximal member 113 of elongated needle member 112, and an intermediary member 121 coupled to and disposed between shaft 119 and proximal member 113 as shown. Release bar 176 defines horizontal grooves 178, 180, 182 which receive respective pins 184, 186, 188 (FIG. 8) of latches 174a, 174b, 174c to allow longitudinal translation of the latches in their respective grooves. Release bar 176 also defines vertical grooves 190, 192 which receive pins 191, 193 connected to housing 152. Pins 191, 193 substantially constrain movement of release bar 176 to the vertical direction relative to housing 152, and also restrict the extent of such vertical movement as shown.

Figure 16A:
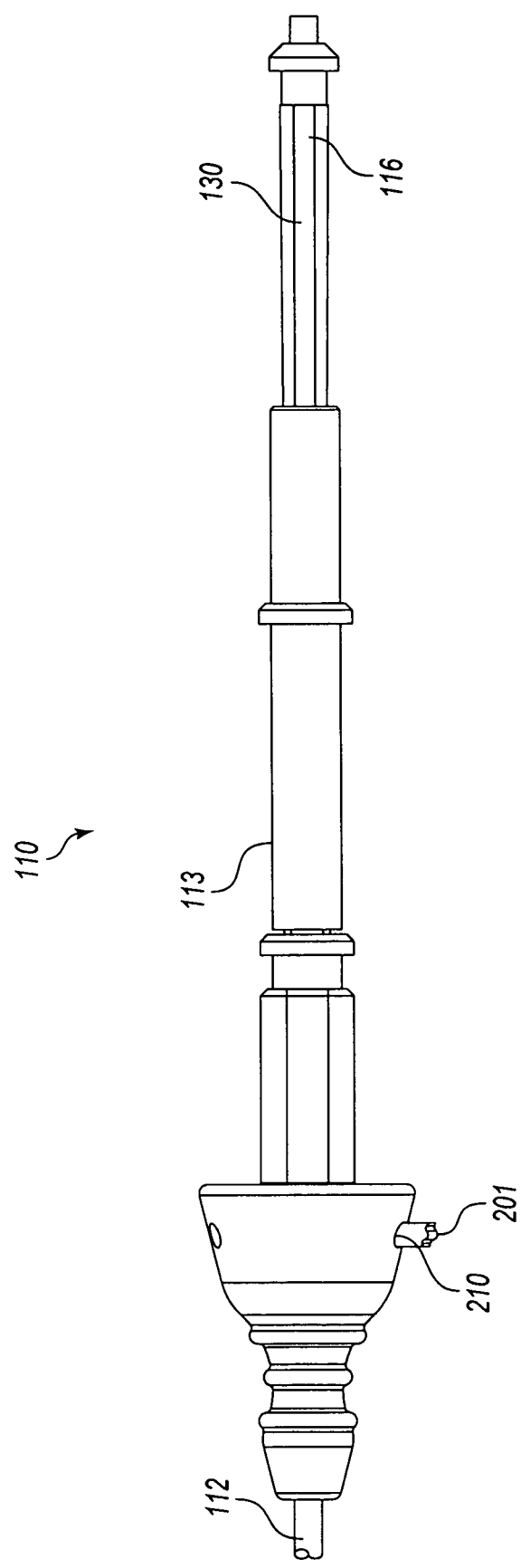
FIG. 16A is an embodiment of a lock pin of the present invention.

Turning to FIGS. 6 and 16A, assembly of one embodiment of the surgical device 100 occurs as follows. Proximal member 130 of disposable needle member 112 is advanced into an aperture (not shown) in rotation hub 154 and into the interior of the housing 152 via aperture 153. Proximal end 132 encounters latch 174c, which rotates clockwise (as sloped surface 175 is pushed upward by proximal end 132) to allow entry of proximal member 130. It will be appreciated that release bar 176 is biased upward by vertical spring 177, which biases latches 174a, 174b, 174c toward counter clockwise rotation toward their original position when they are rotated clockwise. Proximal end 132 is fed through sliding shaft 122 of housing assembly 150, and advanced proximately until it reaches distal end 155 of retraction slide 166, which is operatively disposed in a forward position as shown in FIG. 6. When proximal end 132 reaches distal end 155 of retraction slide 166, it clicks into place between distal end 155 and latch 174a as latch 174a closes around the enlarged head thereof.

It will be appreciated that when proximal end 132 of proximal member 130 of grasping assembly 116 reaches distal end 155 of retraction slide 166, the radially enlarged head 117 of proximal member 113 of elongated needle member 112 interfaces to sliding shaft 122 of handle assembly 150, and also snaps into place between latch member 174b and sliding shaft 122. In this manner, both the inner grasping assembly 116 and outer needle member 112 are positioned and operatively coupled to handle assembly 150 for independent control thereof. The assembled configuration of FIG. 6 corresponds to that shown in FIG. 5, in which the arms 124, 126 of the grasping assembly 116 are exposed and act as an obturator relative to the distal tip 118 to help prevent accidental trauma with the distal tip 118. In this configuration, trigger 158 has been pulled back and ratcheted in place via ratchet 159 to keep arms 124, 126 in a closed position. It is anticipated that the surgical device 100 could be shipped in this configuration with one disposable needle assembly 110 already assembled therein. Alternatively or additionally, the surgical device 100 could be shipped with a single handle assembly 150 and one or more separate disposable needle assemblies 110 separately contained in the same or different packaging.

Returning to FIG. 6 with continued reference to FIGS. 2, 4, 5 and 9, operation of one embodiment of the device 100 occurs as follows. Button 194 (best shown in FIG. 9) is depressed by a user (e.g., a surgeon), causing rim 194a to deploy from groove 195 defined in retraction slide 166 to ride along edge 181 of retraction slide 166. Retraction slide 166 may then be pulled proximally against the bias of spring 168 until rim 194a reaches secondary groove 197 and snaps therein. This motion pulls slide 166 to the retracted position of FIG. 4, which directly pulls arms 124, 126 of grasping assembly 116 fully into needle member 112 to expose distal tip 118 as shown in FIG. 1. At this point, the device is armed, and the distal tip 118 is advanced into the patient to a surgical site. Once the surgical site is reached, button 194 is depressed, and spring 168 pulls slide 166 back to the forward position of FIG. 7, which corresponds to the advanced open configuration of the arms 124, 126 in FIG. 2. Rotation hub 154 may be utilized to rotate grasping assembly 116 and needle member 112 as needed independent of housing assembly 150, and the entire assembly may additionally be manipulated by the surgeon as needed to establish a desired orientation of arms 124, 126 about target tissue in the patient. Finally, ratchet 159 is disengaged, and trigger 158 is pulled to distally advance sliding shaft 122, and thus needle member 112 over the grasping assembly 116 to close and clamp arms 124, 126 about the target tissue. It will be appreciated that arms/jaws 124, 126 remain in a fixed longitudinal position relative to the patient during closing thereof, which can be advantageous to the surgeon to avoid unwanted motion or displacement.

Once the elongated needle member 112 is removed from the patient, release lever 170 (FIGS. 6, 8) is operated to vertically raise release bar 176, which vertically raises latches 174a, 174b, 174c to provide clearance for removal of disposable needle assembly 110 through aperture 153. Disposable assembly 110 (FIG. 16A) is pulled distally through aperture 153 (FIG. 7) for removal and discarding thereof. A new disposable assembly can subsequently be used with the reusable handle assembly 150. The handle assembly 150 may be steam sterilized or sterilized through any other suitable and appropriate manner known in the art.

Figure 16B:
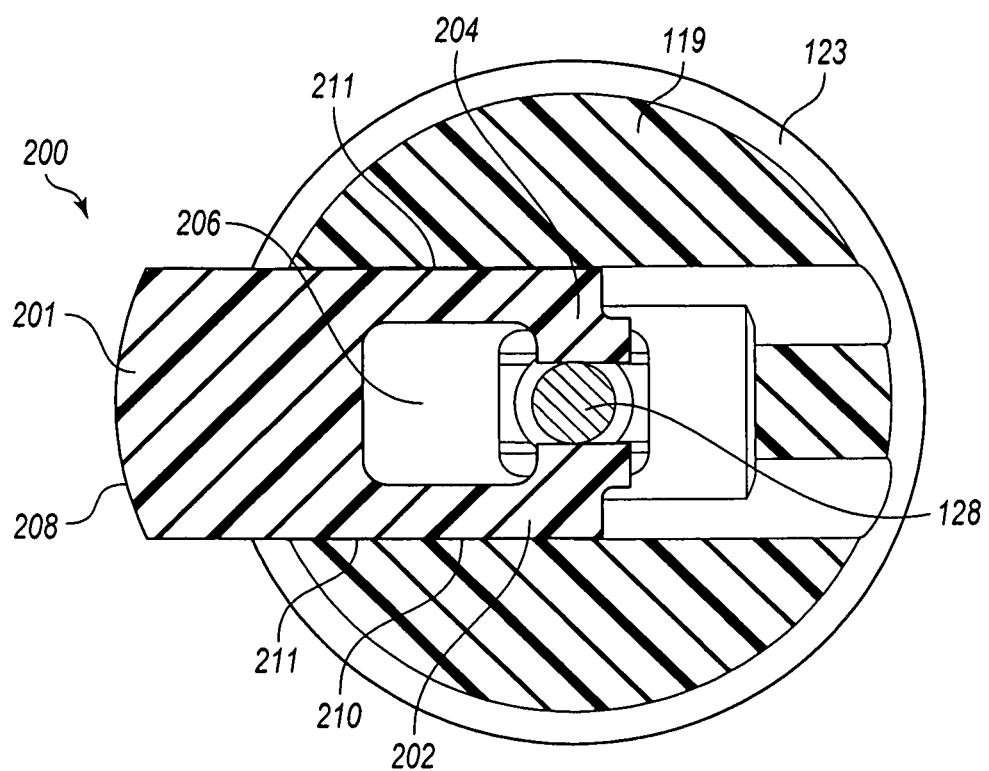
FIG. 16B is an embodiment of a lock pin of the present invention.
Figure 16C:
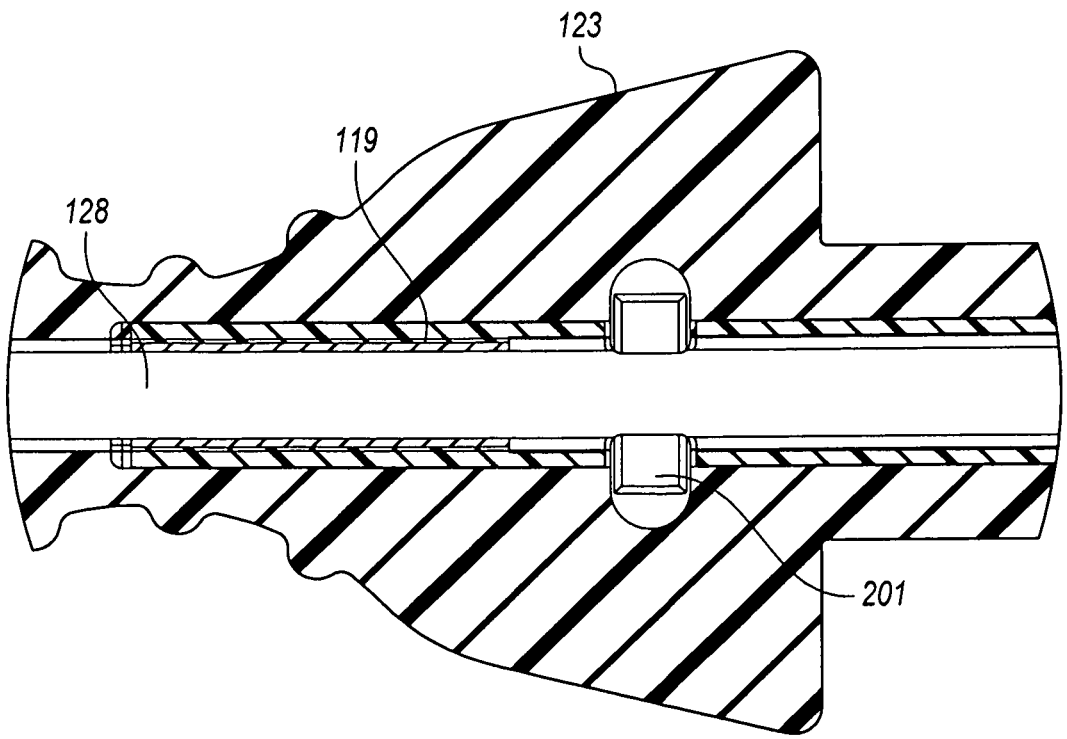
FIG. 16C is an embodiment of a lock pin of the present invention.
Figure 16D:
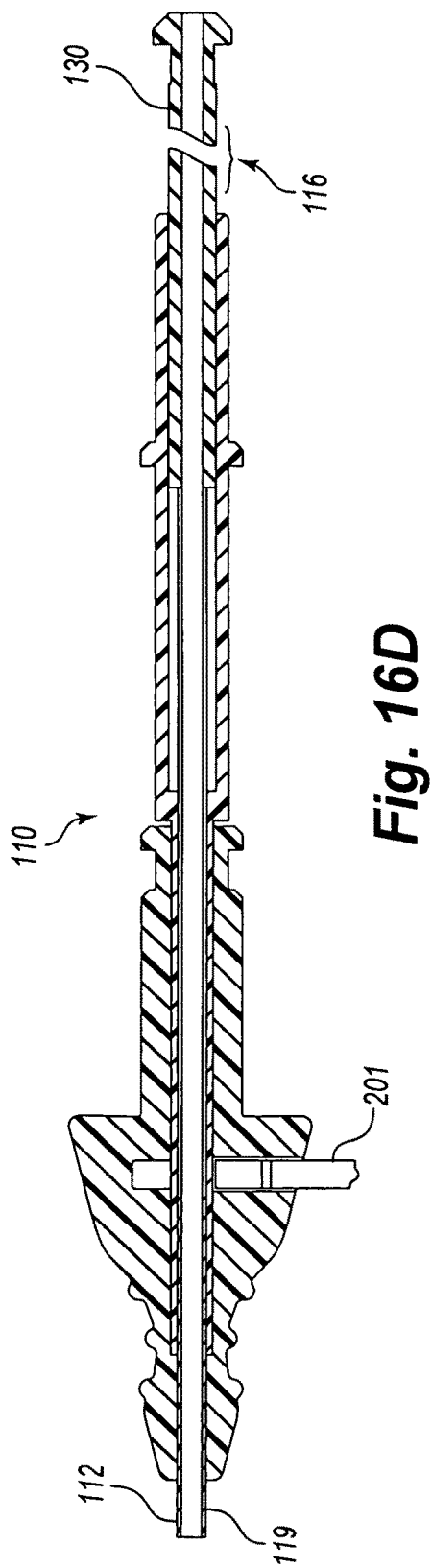
FIG. 16D is an embodiment of a lock pin of the present invention.

Turning now to FIGS. 16A-16D, in one embodiment of the invention, the disposable needle assembly 110 includes a push button assembly 200 and associated structure which prevents longitudinal translation of grasping assembly 116 relative to needle member 112 when button 201 is operatively disposed in an unpressed radially outward configuration. As shown, push button 201 is configured and adapted to be radially translated from the radially outward position to a radially inward position. In the radially outward position, flanges 202, 204 interface to shaft 128 (e.g., via interference fit) of grasping assembly 116 to prevent distal longitudinal translation of shaft 128 relative to shaft 119 of elongated needle member 112. As shown in FIG. 16B, button 201 defines a cutout 206 situated to provide a passage for longitudinal translation of shaft 128 when button 201 is depressed into the radially inward position. Button 201 preferably extends into needle hub 114, and defines an arcuate outer surface 208 which is radially aligned with or radially inward of outer surface 123 of needle hub 114 when button 201 is depressed to the radially inward position. Additionally, side surface 211 of button 201 preferably forms an interference fit with inner surface 210 (FIG. 16A) of needle hub 114 such that significant pressure is needed to depress button 201. In this manner, once depressed, button 201 becomes stuck in the depressed position and cannot be moved radially outward because all surfaces thereof are firmly wedged within needle hub 114.

It will be appreciated that button assembly 200 prevents needle assembly 110 from accordion folding when inserted into reusable handle assembly 150 (e.g., prevents grasping assembly 116 and components thereof from translating distally relative to elongated needle member 112 when disposable needle assembly 110 is inserted into handle assembly 150). It will also be appreciated that once disposable needle assembly 110 is inserted into handle assembly 150, button 201 may be depressed to allow distal translation of grasping assembly 116 to operate the device 100.

Button assembly 200 also functions to help prevent unauthorized re-use, re-selling, or replication of disposable needle assembly 110 by virtue of the inability to longitudinally lock the components of the needle assembly 110 (e.g., for loading the needle assembly 110 into the handle assembly 150) once button 200 is pushed, and the inability to take apart disposable needle assembly 110.

It will be appreciated that the internal mechanisms of the handle assembly 150 described above may alternatively be accomplished using a more simplified structure having less moving parts. For example, elongated needle 112 may be configured as one integrated piece of uniform diameter extending from distal tip 118 to proximal end 115, and grasping assembly 116 may similarly be configured as one integrated piece extending from arms 124, 126 to proximal end 132. For example, one or two latches may be utilized instead of three, and structure different from the latches and sliding shaft disclosed above may be utilized to interface to elongated needle 112 and grasping assembly 116.

Figure 17:
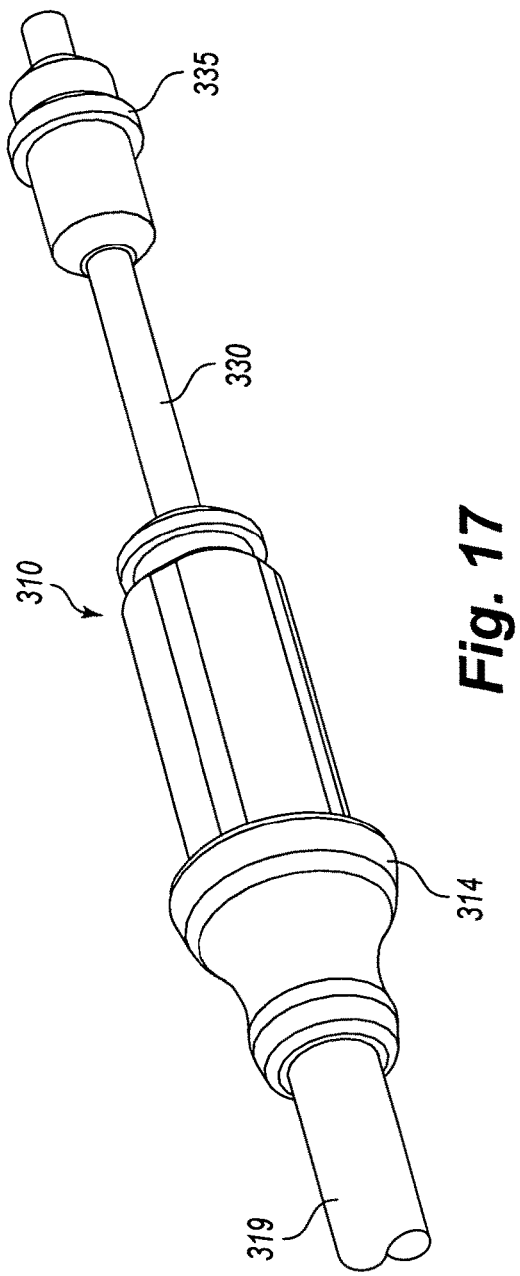
FIG. 17 is an embodiment of a lock pin of the present invention.

Turning to FIG. 17, a disposable needle assembly 310 is shown which includes a conventional 5 mm device. Disposable needle assembly 310 includes a shaft 319 configured to be inserted through a standard trocar, hub assembly 314 configured and adapted to be coupled and longitudinally fixed to housing assembly 150, and proximal inner shaft 330 which longitudinally translates within shaft 319 and hub assembly 314. As shown, inner shaft 330 contains a radially enlarged rim 335 which couples to sliding shaft 122 of housing assembly 150. In this manner, trigger 158 of housing assembly 150 may be utilized to directly translate the inner rather than the outer components of the disposable assembly. In such 5 mm embodiments, it will be appreciated that shaft 319 is longitudinally fixed to hub assembly 314, and that only inner shaft 330 moves relative thereto. Button assembly 200 is preferably provided to disposable needle assembly 310 in order to prevent longitudinal translation of the components thereof during loading into housing assembly 150 as discussed above.

Figure 11:
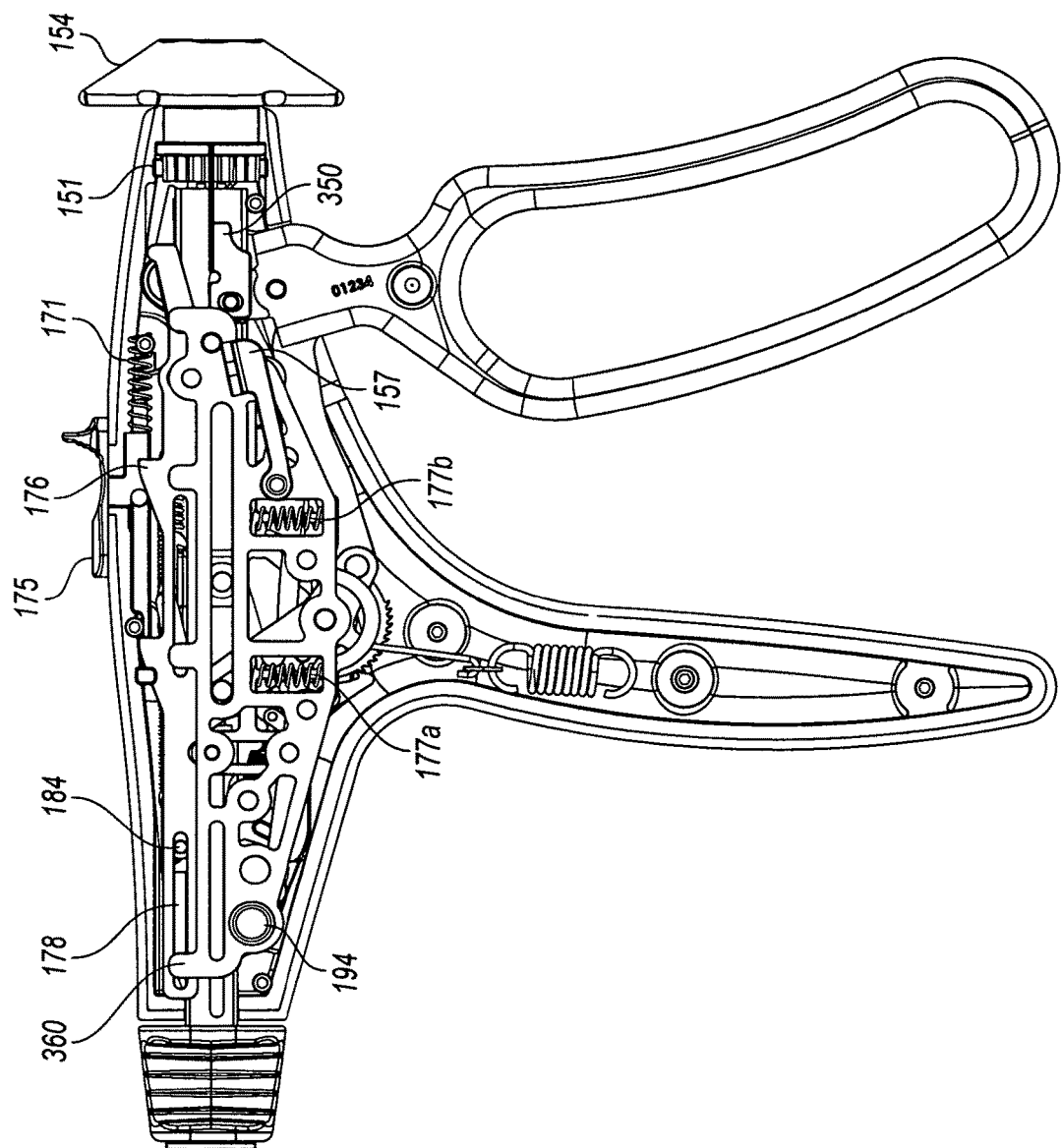
FIG. 11 is an embodiment of the reusable handle assembly of the present invention.

A further embodiment of the handle assembly 150 of the present invention is shown in FIGS. 10-15. FIGS. 10 and 11 show two sides of a further embodiment of the handle assembly 150 of the present invention wherein the trigger motion of the trigger 158 when compressed causes a rotational motion of the crank assembly 162 which causes linear motion of the elongated needle member 112. In this embodiment the trigger 158 is of different configuration than that shown in FIGS. 6 and 7. In FIGS. 10 and 11 trigger 158 is of an open trigger with movement limited by a trigger lock (shown in FIGS. 12A and 12B). The trigger lock 340 includes a trigger lock link 346 and rotational lock such that when the button 201 is pushed inward by the user (e.g., surgeon) the trigger lock 340 locks in the trigger 158 in a depressed state with the grasping assembly 116 in a closed position. The handle assembly includes a cage comprised of a right cage 360 and left cage 361 which defines the inner workings of the handle assembly 150.

Continuing with FIGS. 10 and 11, handle assembly 150 further includes a primary return spring 164 for biasing sliding trigger 158 distally toward the configuration of FIG. 1 in which the arms 124, 126 of the grasping assembly 116 are extended relative to the needle member 112 and open. Handle assembly 150 also includes an arm slide 166 for manipulating elongated needle member 112. Handle assembly 150 also includes a release switch 175 and release spring 171 for allowing release of disposable assembly 110 from handle assembly 150 and a latch assembly for receiving, positioning, operating, and releasing elongated needle member 112 from the guide box 179 within handle assembly 150. The guide box 179 is configured to match the configuration of the proximal member 130 of the disposable needle assembly 110 such as, for example, both the guide box 179 and proximal member 130 being configured in the shape of a rectangle or square or circle or oval or any other corresponding geometric shape.

Figure 12B:
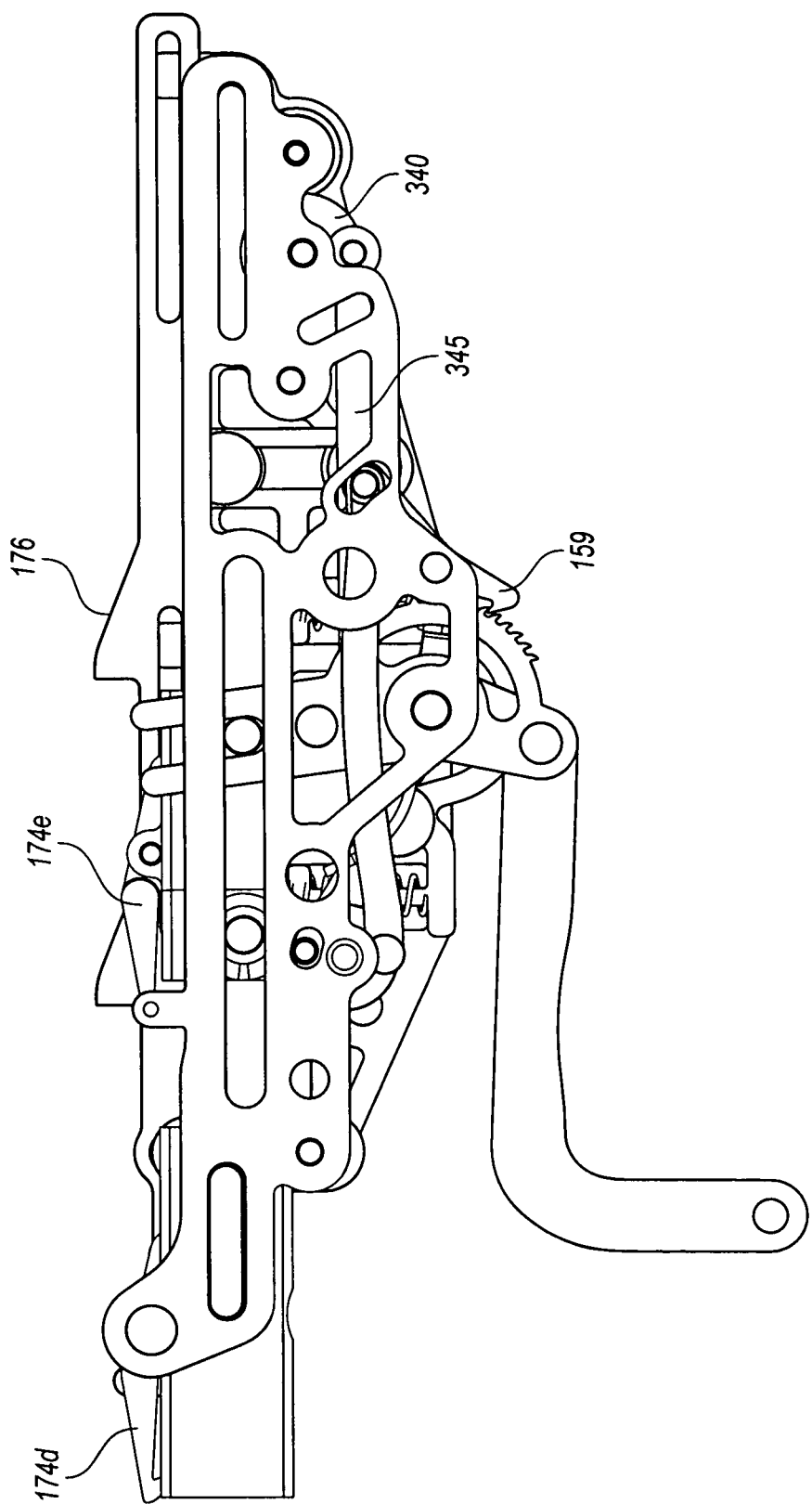
FIG. 12B is a side plan of a cage assembly embodiment of the reusable handle assembly of the present invention.
Figure 12C:
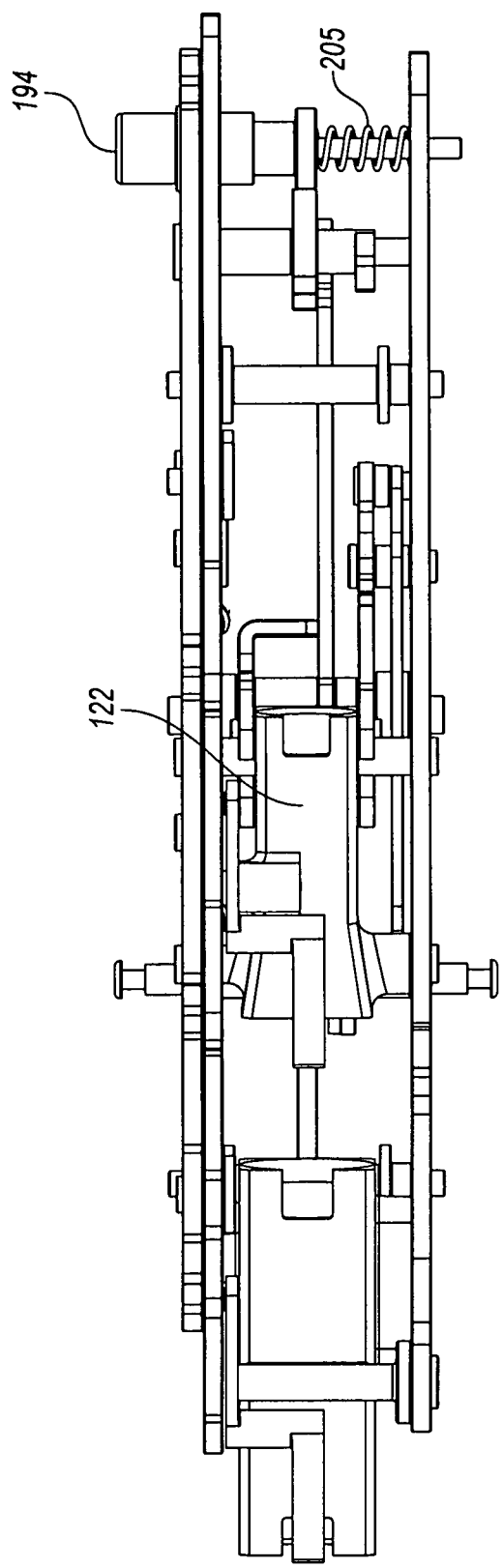
FIG. 12C is a perspective of a cage assembly embodiment of the reusable handle assembly of the present invention.
Figure 13B:
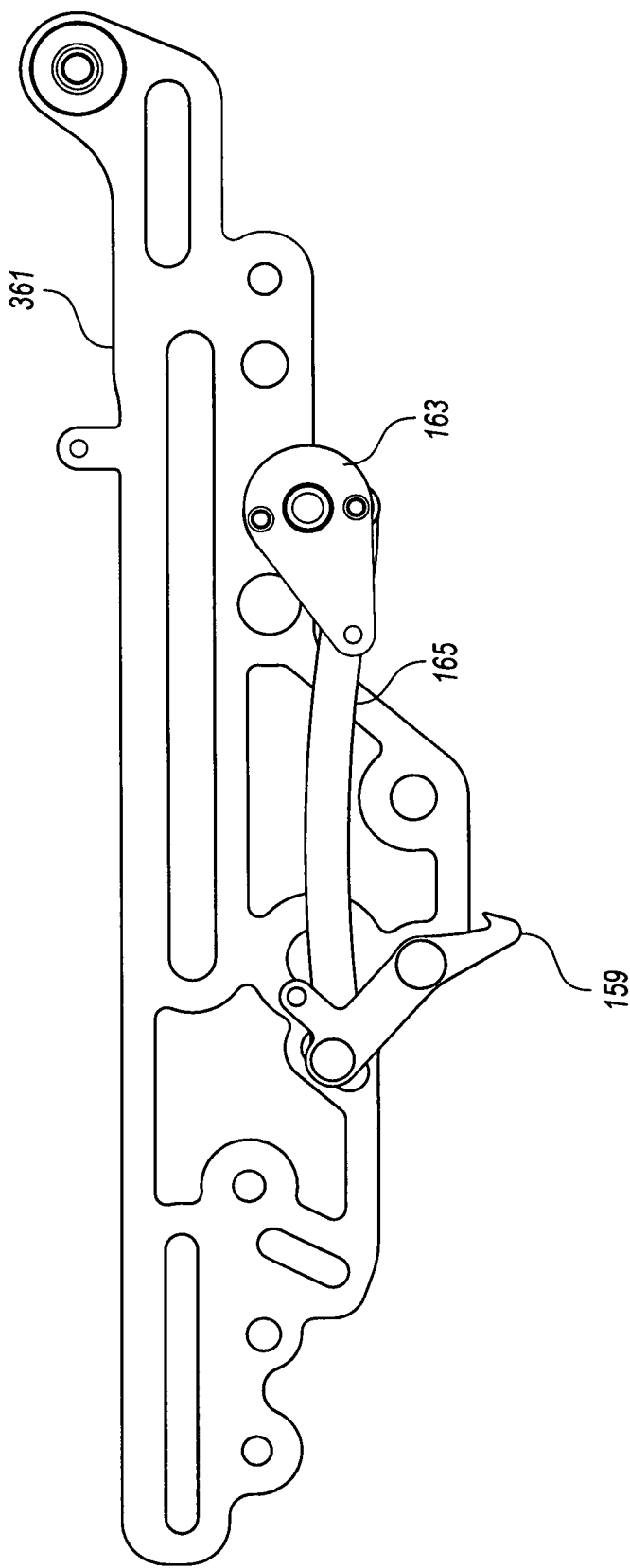
FIG. 13B is a side plan of a ratchet mechanism embodiment of the reusable handle assembly of the present invention.
Figure 14:
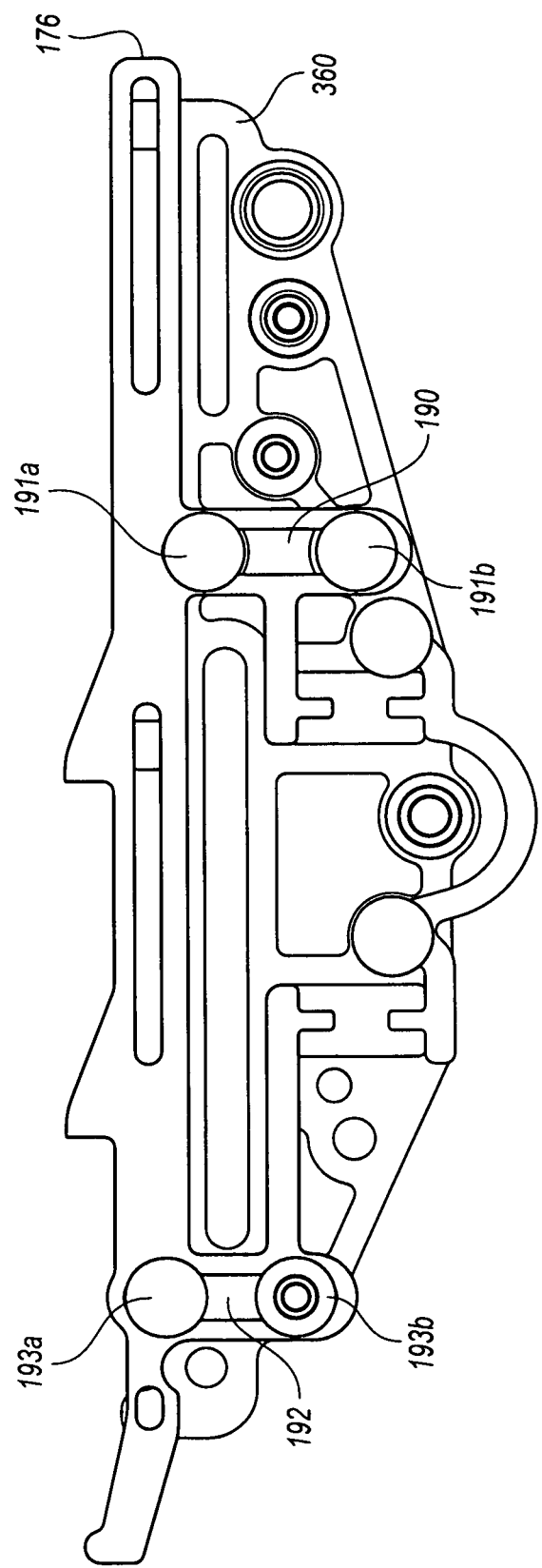
FIG. 14 is a side plan of a ratchet mechanism embodiment of the reusable handle assembly of the present invention.

As shown in more detail in FIGS. 12A and 12B, the latch assembly includes latches 174d and 174e, which are found on right cage 360, and release bar 176, which, in conjunction with release spring 171, operate to vertically raise and lower latches 174d and 174e to receive and release the disposable assembly 110. Release bar 176 defines horizontal grooves 178 and 180 which receive respective pins 184 and 186 of latches 174d and 174d to allow longitudinal translation of the latches in their respective grooves. As shown in FIG. 14, release bar 176 on right cage 360 also defines vertical grooves 190, 192 which receive pins 191a, 191b, 193a and 193b connected to housing 152. Pins 191a, 191b, 193a and 193b substantially constrain movement of release bar 176 to the vertical direction relative to housing 152, and also restrict the extent of such vertical movement as shown.

The handle assembly 150 includes a ratchet mechanism so as to prevent trigger and needle return throughout the full jaw closure stroke. In one embodiment the ratchet mechanism has audible and tactile clicks during actuation. The ratchet mechanism may have a number of lock positions and in one embodiment has a minimum of nine (9) lock positions throughout the full jaw closure stroke. The final ratchet position may correspond with the fully closed jaw safe position. Turning to FIGS. 10, 13A, 13B and 15, a ratchet 159 is shown as activated by a ratchet switch 157. The ratchet switch 157 allows the ratchet mechanism to be turned on and off to disengaged the ratchet and allow free opening of the jaws upon manual release of the trigger 158. The ratchet switch 157 is found on both sides of the handle assembly 150 and may be actuated by the thumb of the user. The up switch position corresponds with the ratchet mode, the down position corresponds to the free mode. The switch shaft 161 is connected to the switch spring level 163 activated by the switch link 165 and switch spring 167. The ratchet spring 169 is connected to the ratchet switch 157. A switch spring 167 drives the switch to its final ratchet or free positions to prevent the switch from residing in an intermediate position. Switch actuation will have an audible and tactile click when in use. A temporary ratchet release trigger resides forward of the main trigger and is to be actuated by the index finger. The temporary release trigger allows the ratchet to be released when it is squeezed when the device is in the ratchet mode. It will have a spring return and will reengage the ratchet when it is released.

Another feature of this embodiment of the handle assembly 150 of the present invention is the rotational hub 154. When the proximal member 130 of disposable elongated needle member 112 is advanced into an aperture (not shown) in rotation hub 154 and into the interior of the housing 152 via the guide box 179 there is a rotation detent spring 151 which provides an audio cue to the user (e.g., surgeon) that the needle member 112 is moving such that there are clicks generated via the spring 151. Continuing with the actuation of the present invention, when proximal end 132 encounters latch 174d, such latch rotates clockwise (as sloped surface 175 is pushed upward by proximal end 132) to allow entry of proximal member 130. It will be appreciated that release bar 176 is biased upward by vertical spring 177, which biases latches 174d and 174e toward counter clockwise rotation toward their original position when they are rotated clockwise. Proximal end 132 is fed through sliding shaft 122 of housing assembly 150, and advanced proximately until it reaches distal end 155 of retraction slide 166, which is operatively disposed in a forward position (not shown in FIGS. 10 and 11). When proximal end 132 reaches distal end 155 of retraction slide 166, it clicks into place between distal end 155 and latch 174d as latch 174d closes around the enlarged head thereof. It will be appreciated that when proximal end 132 of proximal member 130 of grasping assembly 116 reaches distal end 155 of retraction slide 166, the radially enlarged head 117 of proximal member 113 of needle member 112 interfaces to sliding shaft 122 of handle assembly 150, and also snaps into place between latch member 174e and sliding shaft 122. In this manner, both the inner grasping assembly 116 and outer needle member 112 are positioned and operatively coupled to handle assembly 150 for independent control thereof.

In operation button 194 is depressed by a user (e.g., a surgeon), causing as shown in FIG. 21, push button spring 205 to compress allowing sliding shaft 122 to deploy. Retraction slide 166 may then be pulled proximally against the bias of spring 168 and this motion pulls arms 124, 126 of grasping assembly 116 fully into needle member 112 to expose distal tip 118 as shown in FIGS. 3 and 4. At this point, the device is armed, and the distal tip 118 is advanced into the patient to a surgical site. Once the surgical site is reached, button 194 is depressed, and spring 168 pulls slide 166 back to the forward position and to the advanced open configuration of the arms 124, 126 in FIGS. 1 and 2. Rotation hub 154 may be utilized to rotate grasping assembly 116 and elongated needle member 112 as needed independent of housing assembly 150, and the entire assembly may additionally be manipulated by the surgeon as needed to establish a desired orientation of arms 124, 126 about target tissue in the patient. Finally, ratchet 159 is disengaged, and trigger 158 is pulled to distally advance sliding shaft 122, and thus elongated needle member 112 over the grasping assembly 116 to close and clamp arms 124, 126 about the target tissue. It will be appreciated that the grasping arms 124, 126 remain in a fixed longitudinal position relative to the patient during closing thereof, which can be advantageous to the surgeon to avoid unwanted motion or displacement. The arm slide 166 may only be actuated when the trigger 158 is fully closed and each mechanism is separate.

Once the elongated needle member 112 is removed from the patient, release switch 175 is operated to vertically raise release bar 176, which vertically raises latches 174d and 174e to provide clearance for removal of disposable needle assembly 110 through aperture 153. A new disposable assembly can subsequently be used with the reusable handle assembly 150. Other end effectors of the disposable assembly may be used such as scissors, grabbers, clasps, staplers, needle holders, cauterizers and other known end effectors. If graspers are chosen the graspers may include configurations of babcock, alligator, clutch and bowel style jaws and other known variants. The handle assembly 150 may be steam sterilized or sterilized through any other suitable and appropriate manner known in the art.

If a disposable assembly is monopolar then the arm includes additional components. A typical electrosurgical treatment instrument is capable of treating tissue with the use of heat produced by electrical energy while cutting, shearing, grasping, or contacting the tissue. Such instruments are used to carry out treatments, such as incision, coagulation, and the like. During such a procedure instrument or device would be equipped with an active electrode and an inactive, so-called neutral electrode. During the whole duration of the surgery, the neutral electrode is electrically connected to a large area of the skin of the patient, for example, to the thigh or the upper arm. The surgical instrument interface may further comprise an electrical connector for connecting the conductor to an external electrosurgical generator. Electrical energy may be supplied to the surgical instrument by a conventional electrosurgical which the user (e.g., surgeon) may activate via a foot switch electrically connected to the electrosurgical generator, causing the generator to supply electrical energy through a power cord and the connector to the instrument. Typically a high frequency AC or RF current may be employed, with the voltage being dependent on the type and degree of treatment desired. Voltages may range up to at least 12,000V in some cases, with about 3000V being a typical value, e.g., for coagulation.

Figure 18A:
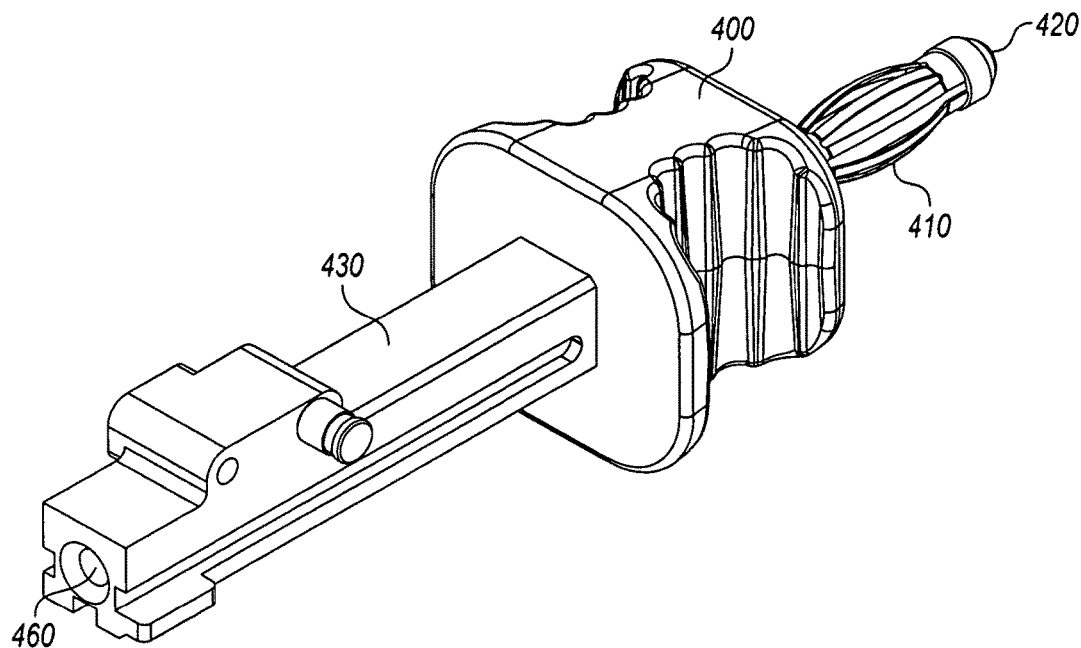
FIG. 18A is an embodiment of a monopolar arm slide of the present invention.
Figure 18B:
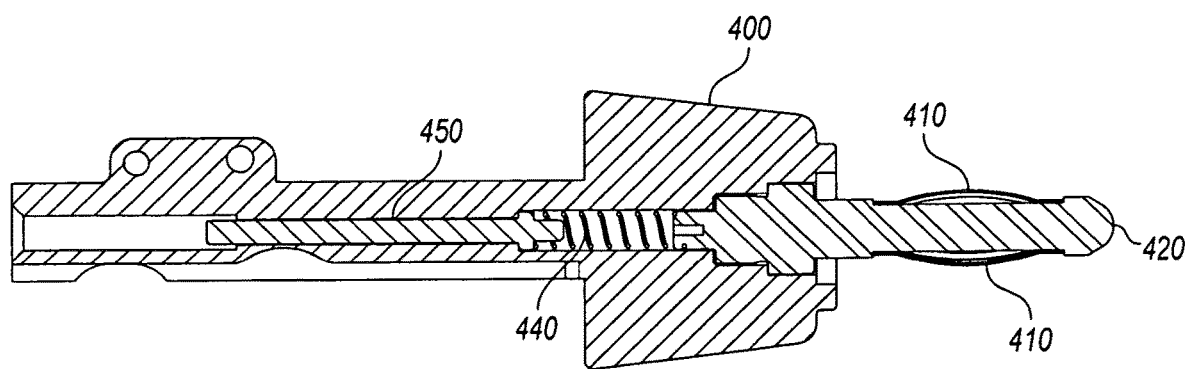
FIG. 18B is an embodiment of a monopolar arm slide of the present invention.
Figure 19A:
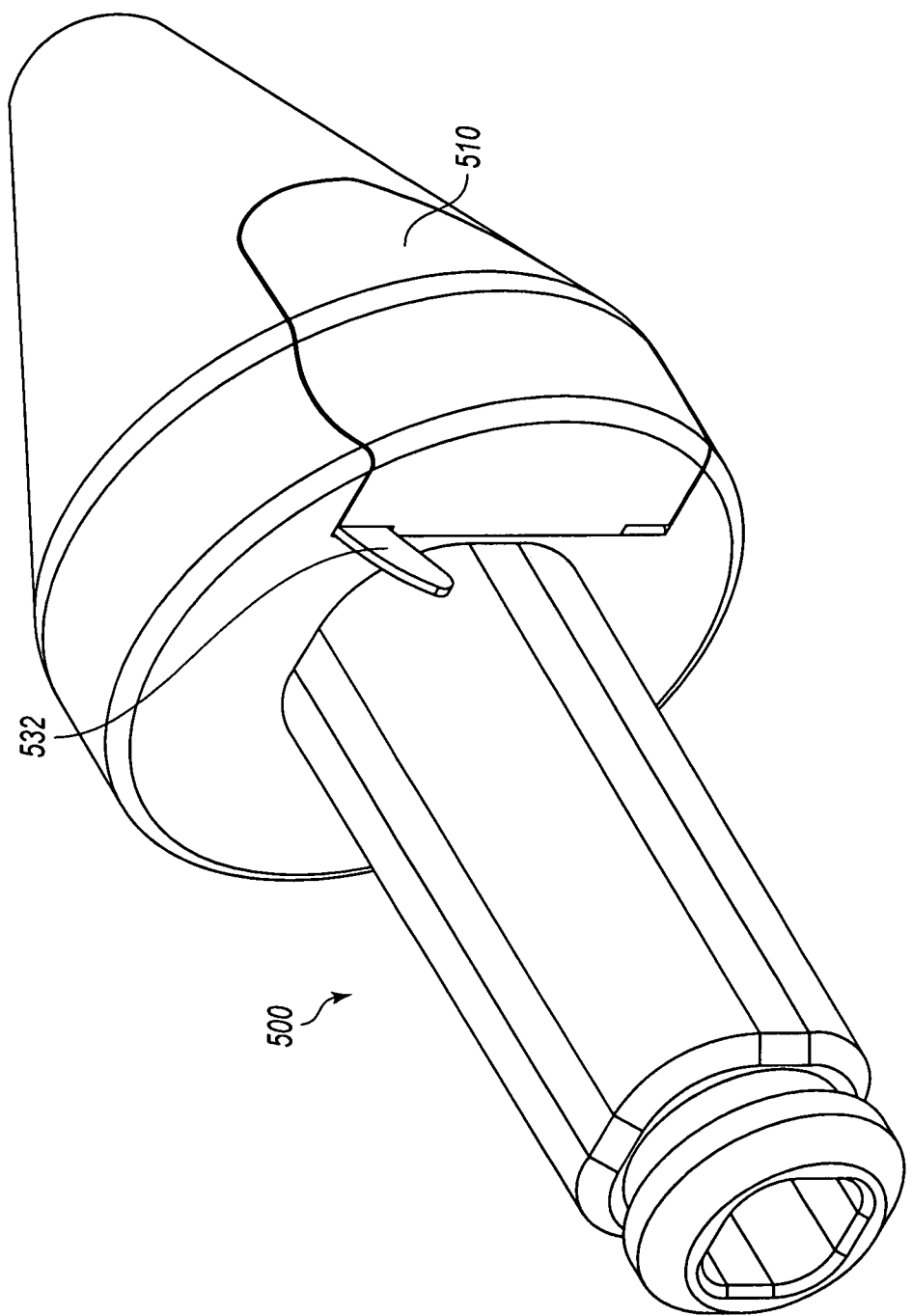
FIG. 19A is an embodiment of a cap on a disposable needle assembly of the present invention.
Figure 19B:
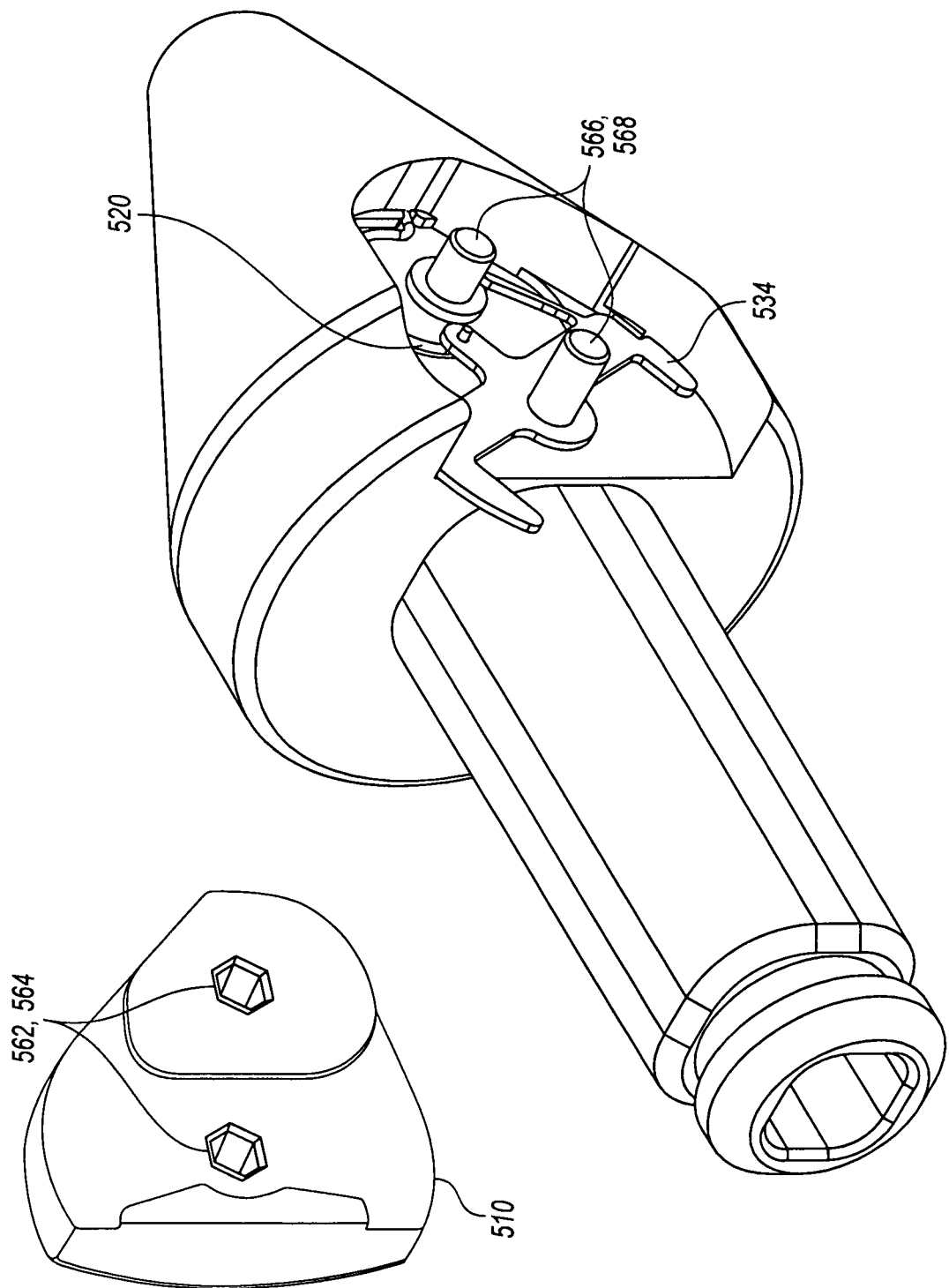
FIG. 19B is an embodiment of a cap on a disposable needle assembly of the present invention.
Figure 19C:
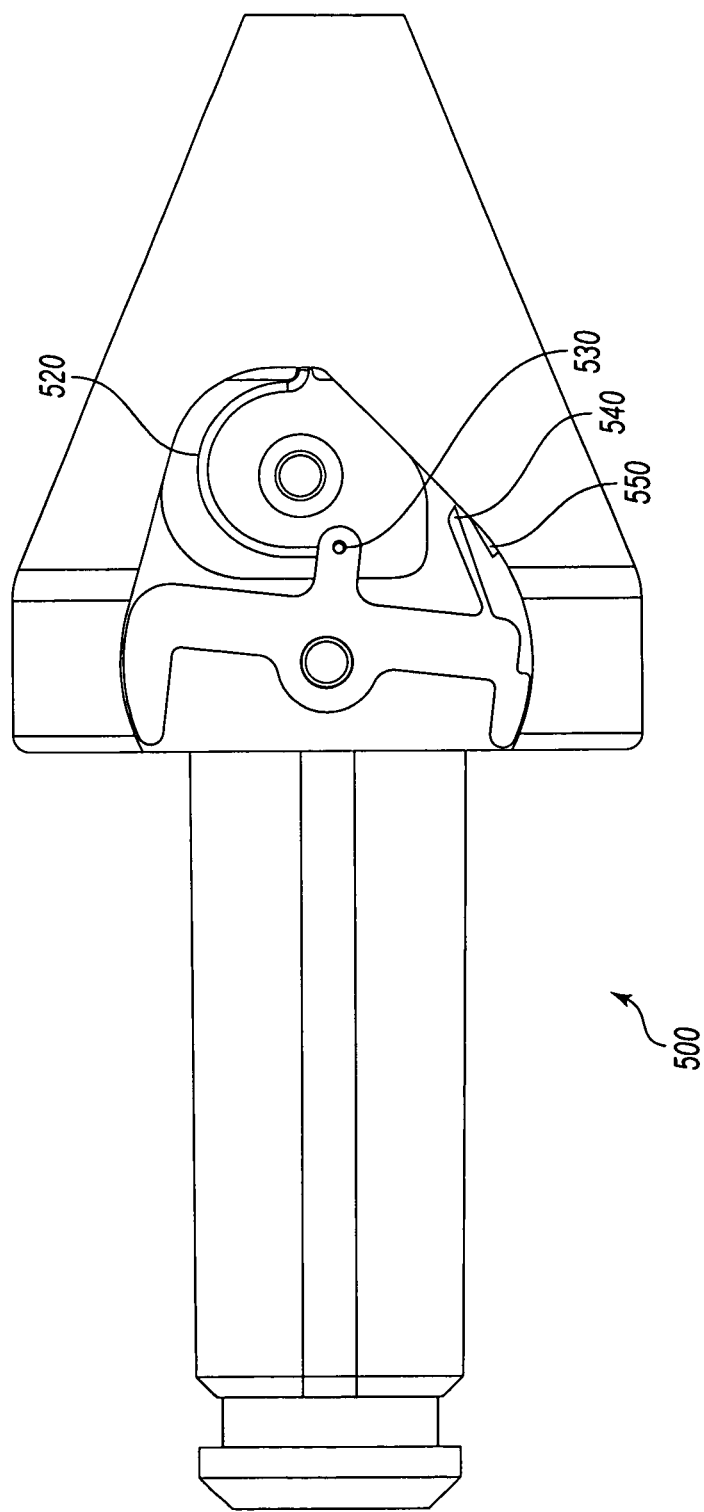
FIG. 19C is an embodiment of a cap on a disposable needle assembly of the present invention.
Figure 19D:
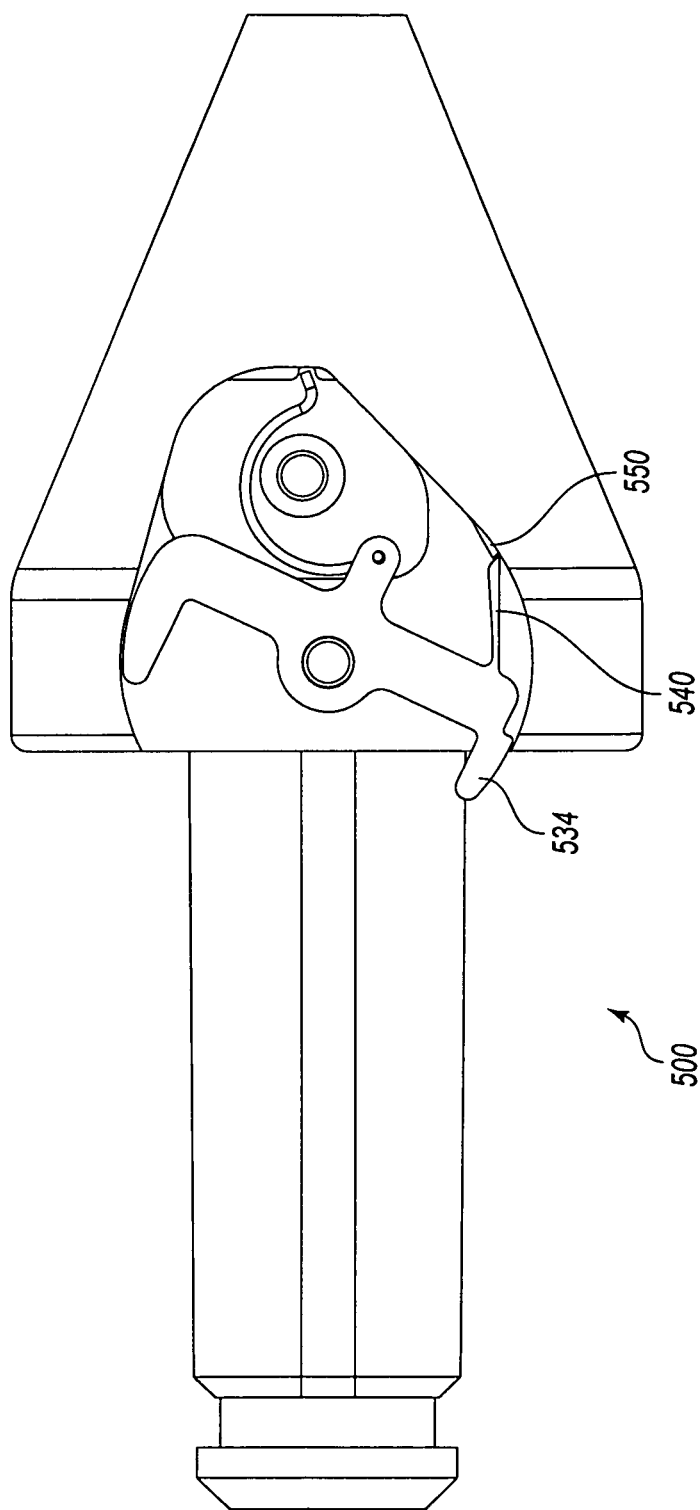
FIG. 19D is an embodiment of a cap on a disposable needle assembly of the present invention.

As shown in FIGS. 18 (18A and 18B) a monopolar arm 400 includes a contact post 420 having a cage 410 of a plurality of spiral loops. The contact post 420 is connected to an electrical source as described above. The monopolar arm 400 further includes a monopolar arm slide 430 which has an aperture 460 for insertion of the disposable needle assembly 110 or any other disposable assembly capable of activation via electrical energy. The monopolar arm 400 further includes monopolar spring 440 and contact plunger 450 so that when the disposable needle assembly 110 is inserted into the aperture 460 it exerts a force on the contact plunger 450 which compresses contact spring 440 and the electrical energy is transferred via contact post 420 to the disposable needle assembly 110.

The present invention allows for a single reusable handle assembly 150 into which many types of disposable assemblies may be inserted, locked, actuated and then released for disposable. It will be appreciated that separation of the needle and handle assemblies 110, 150 described above will also allow the needle assemblies to be melted down and recycled, and the handles to be sterilized and reused. Additionally, it will be appreciated that the access surface area provided by a 5 mm trocar is approximately 24.6 mm.sup.2 whereas that provided by the 2.4 mm needle is approximately 4.5 mm.sup.2, which represents an 82% reduction in access surface area, meaning no stitching or scars, less pain, and a quicker recovery for the patient. Further, the device may be inserted percutaneously under direct visualization by the surgeon without the use of a trocar, resulting in a shorter surgery with less tissue trauma and scars.

In one embodiment of the present invention as shown by FIGS. 19A, 19B, 19C and 19D, the needle assembly includes a lock hub assembly 500 which includes a cap 510 covering an internal lock spring 520 attached to a lock pivot 530 which has an upper distal end 532 and lower distal end 534 each of which is capable of protruding from the cap 510 and is capable of moving in one direction. In use, the lock pivot 530 is actuated when the needle assembly 110 is inserted into and then released from the handle assembly 150. Upon insertion of the needle assembly 110 into the handle assembly 150 the lock pivot 530 rotates such the upper distal end 522 which was protruding from the cap 510 now resides within the cap 510. Upon release from the handle assembly 150 the lock pivot 530 further rotates but is stopped by the cap 510 actuating a lock bar 540 which locks into a latch 550 within the cap 510. The lower distal end 534 of the lock pivot 530 thus protrudes from the cap 510. In this position the disposable needle assembly 110 cannot be reused resulting in a safety feature. The cap 510 is attached to the lock hub assembly 500 via at least one, preferably two, apertures 562, 564 in the cap 510 which attach to a corresponding male member 566, 568 located within the lock hub assembly 500.

The inventive surgical device includes a trigger 158 design in which the pistol grip style has a fixed palm grip and pivoting finger actuated trigger such that the trigger may wrap around the middle and ring finger for use with smaller hands whereas the surgeon with larger hands may grip the outer surface of the wrap around trigger 158. In some embodiments of the trigger 158 finger indents may be provided. The trigger 158 in use may thus be used by either right handed surgeons and left handed surgeons. Further, in use the inventive device is capable of being operated single-handedly, with the exception of loading and releasing the disposable assemblies.

Further, the inventive device has the advantages of an unloaded handle having a trigger and arming slide locked in position ready to accept new assemblies such as a needle assembly having different end effectors. The disposable assembly may only be released in a safe position with for instance if using a grasper, fully closed jaws it is anticipated that such a release switch mechanism to be useful for a minimum of 1000 cycles.

Further safety features include the arm slide 166 extending from the back of the handle assembly 150 which must be pulled forward with the user's for instance thumb and index finger by a gripping surface to retract for instance the grasping arms or jaws completely into the disposable needle member 112 and fully expose the needle tip 118. In use the user's nominal arming stroke may be about 0.620. Upon complete arming the arm slide 166 actuation a latch mechanism which automatically locks the device in the armed position. A red visible indicator shows that the needle assembly 110 is armed and that the sharp needle tip 118 is exposed. A button located toward the rear of the left side of the handle assembly 150 is to be depressed to spring return the needle assembly 110 to the safe position with the needle tip 188 retracted within the elongated needle member 112. In one embodiment a nominal return spring load at the armed position is capable of driving the grasper arms 124, 126 out of the needle assembly 110 and is 2.4 pounds of weight or force. It is anticipated that such an arming mechanism to be useful for a minimum of 1000 cycles.

Another safety feature of the present invention is the rotation hub 154 which may include with light resistance to prevent an inadvertent rotation of the grasping assembly 116. In use the rotation hub 154 has a tactile resistance and audible clicks heard by the user to indicate the rotations. There is a range of continuous rotation in both directions of the rotation hub 154 allowing the user ambidextrous operation of all functions during surgery except there is a lock during insertion and release of the assembly. The rotation lock is actuated during trigger actuation so as to allow rotational manipulation of grasped tissue without the need to manually restrain the rotation hub 154.

Yet another safety feature of the present invention includes the trigger 158 actuation which requires force to overcome the primary return spring 164 to advance needle tip 118 over axially fixed graspers 124, 126. In one embodiment of the present invention the nominal needle actuation stroke from the safe position to the end effector fully open position is 0.690. In one embodiment of the present invention a complete spring return of trigger and needle is required for the needle assembly 110 with a range of nominal return spring load at the safe position of about 1.3 pounds. It is anticipated that such a trigger 158 actuation mechanism may be useful for a minimum of 7500 cycles.

A further safety feature of the present invention includes a ratchet switch 157 or ratchet mechanism 159 which may prevent the trigger 158 and needle tip 118 return throughout the full actuation and closing of the graspers 124, 126. The ratchet 159 in use may have audible and tactile clicks during actuation. The ratchet 159 may have a minimum of for instance a range of about three (3) to about ten (10) lock positions throughout the full graspers 124, 126 closure stroke. The final ratchet 159 position may correspond with the fully closed grasping assembly 116 in a safe position. In one embodiment of the present invention, a ratchet switch 157 will allow the ratchet 159 to be turned on and off to disengaged the ratchet 159 and allow free opening of the grasping assembly 116, or any other assembly with other end effectors, upon manual release of the trigger 158 by the user. The ratchet switch 157 may reside on both sides of the handle assembly 150 and thus may be actuated with the thumb of the user. In one embodiment of the present invention the up switch position of the ratchet switch 157 corresponds with the ratchet mode while the down position corresponds to the free mode. A ratchet spring 169 will drive the ratchet switch 157 to either its final ratchet position or free position so as to prevent the ratchet switch 157 from residing in an intermediate position. Such ratchet switch 157 actuation may have an audible and tactile click as a further safety feature for the user. In one embodiment of the present invention a temporary ratchet release trigger may reside forward of the main trigger 158 and may be actuated by the index finger of the user. Such a temporary release trigger will allow the ratchet 159 to be released when the release trigger is squeezed during the time in use when the device is in the ratchet 159 mode. Such an embodiment may have a spring return and will reengage the ratchet 159 when the temporary release trigger is released.

It is anticipated that the life of the handle assembly 150 may exceed more than 350 surgical procedures and corresponding autoclave cycles. The snap-in insertion and release of loading units causes minimal abrasion, and is anticipated to be useful for a minimum of 1,000 cycles.

Further, the handle assembly 150 has the advantage of being configured to receive multiple needle assemblies of varying diameters. For instance the handle assembly may receive and lock a needle assembly having a 5 mm diameter, a 10 mm diameter or other variants. Thus the handle assembly 150 has a universal use with many disposable needle assemblies and even other assemblies without needles.

The following benefits, structure, and advantages are also contemplated by the present invention: reduced surgical time resulting in reduced trauma to the patient and possibly less scarring, easier handling of the device by the user via the more tactile and sturdier handle assembly 150 which handle assembly 150 is capable of multiple types of disposable assemblies, and other benefits.

The methods and systems of the present invention, as described above and shown in the drawings, provide for minimally invasive surgical assemblies with superior properties including ease of assembly, use and operation. While the apparatus and methods of the subject invention have been shown and described with reference to preferred embodiments, those skilled in the art will readily appreciate that changes and/or modifications may be made thereto without departing from the spirit and scope of the subject invention.

REFERENCE NUMERALS

100 surgical device
110 disposable needle assembly
112 elongated needle member
113 lumen
113 proximal member of needle member
114 needle hub
114a proximal portion of hub
114b distal portion of hub
115 proximal head
116 grasping assembly
117 radially enlarged head (of proximal member 113 of needle member 112)
118 sharpened distal tip portion
119 shaft
120 lumen
121 intermediary member
122 sliding shaft
124 grasper upper arm
126 grasper lower arm
128 grasper shaft
130 proximal member
132 proximal end
150 reusable handle assembly
151 rotation spring
152 housing
153 aperture
154 rotation hub
155 distal end (of slide 166)
156 proximal handle member
157 ratchet switch
158 trigger
159 ratchet
160 drive link
161 switch shaft
162 crank assembly
163 switch spring lever
164 primary return spring
165 switch link
166 arm slide (of retraction slide 166)
167 switch spring
168 secondary return spring
169 ratchet spring
170 release lever
171 release spring
174a, 174b, 174c latches on latch assembly 172
175 release switch
176 release bar
177 vertical spring
178, 180, 182 horizontal grooves
179 guide box
181 edge (of retraction slide 166)
184, 186, 188 respective pins 190, 192 vertical grooves
191, 193 pins
194 Button
194a rim (of button 194)
195 groove
197 secondary groove
200 push button assembly
201 button (of button assembly 200)
202, 204 flanges
205 push button spring
206 cutout
208 outer surface (of button 201)
211 side surface (of button 201)
210 inner surface (of hub 114)
310 disposable needle assembly
319 shaft
314 hub assembly
319 shaft
330 proximal inner shaft
335 radially enlarged rim (of shaft 330)
340 trigger lock
345 trigger lock link
350 rotational lock
360 cage right
361 cage left
400 monopolar arm
410 contact cage
420 contact post
430 monopolar slide
440 contact spring
450 contact plunger
460 aperture

What is claimed is:

1. An apparatus comprising:
a disposable needle assembly including a needle shaft having a lumen and an end effector coupled to an end effector shaft extending through the lumen; and
a reusable handle assembly including a housing, a sliding shaft, and a retraction slide,
wherein the disposable needle assembly is insertable into the reusable handle assembly to removably couple the needle shaft to the sliding shaft and to removably couple the end effector shaft to the retraction slide for independent control of the needle shaft and the end effector.

2. The apparatus of claim 1, wherein the reusable handle assembly includes a trigger coupled to the sliding shaft configured to translate the needle shaft.

3. The apparatus of claim 2, wherein the reusable handle includes a ratchet configured to prevent return of the trigger and the needle shaft throughout a stroke.

4. The apparatus of claim 3, wherein the reusable handle includes a ratchet switch configured to disable the ratchet.

5. The apparatus of claim 1, wherein the reusable handle assembly includes a spring that proximally biases the sliding shaft.

6. The apparatus of claim 1, wherein the reusable handle assembly includes a spring that distally biases the retraction slide.

7. The apparatus of claim 1, wherein the reusable handle assembly includes a button configured to disengage a rim from one or more grooves in the retraction slide.

8. The apparatus of claim 7, wherein the button is spring biased, and the one or more grooves includes a first groove configured to engage the rim with the retraction slide in a distal direction and a second groove configured to engage the rim with the retraction slide in a proximal direction.

9. The apparatus of claim 1, wherein the retraction slide includes a portion that extends out of the housing to be manipulated by a user.

10. The apparatus of claim 1, wherein the end effector includes a pair of grasper arms.

11. The apparatus of claim 10, wherein the sliding shaft is configured to push the needle shaft over the pair of grasper arms into a closed configuration.

12. The apparatus of claim 1, wherein the reusable handle assembly includes a plurality of latches configured to receive and release the disposable needle assembly for removal.

13. The apparatus of claim 12, wherein the reusable handle assembly includes a release bar configured to release the plurality of latches from the disposable needle assembly.

14. The apparatus of claim 13, wherein the release bar includes a plurality of horizontal grooves that receive pins of the plurality of latches.

15. The apparatus of claim 13, wherein the release bar includes a plurality of vertical grooves that receive pins connected to the housing.

16. A handle assembly configured to actuate a disposable needle assembly, the disposable needle assembly including a needle shaft having a lumen and an end effector coupled to an end effector shaft extending through the lumen, the handle assembly comprising:
a housing, a sliding shaft, and a retraction slide,
wherein the disposable needle assembly is insertable into the handle assembly to removably couple the needle shaft to the sliding shaft and to removably couple the end effector shaft to the retraction slide for independent control of the needle shaft and the end effector.

17. The handle assembly of claim 16, further comprising a trigger coupled to the sliding shaft and configured to translate the needle shaft.

18. The handle assembly of claim 16, further comprising a spring that proximally biases the sliding shaft.

19. The handle assembly of claim 16, further comprising a spring that distally biases the retraction slide.

20. The handle assembly of claim 16, further comprising a button configured to disengage a rim from one or more grooves in the retraction slide.

* * * * *